United States Patent
Kokubo et al.

(10) Patent No.: US 11,058,509 B2
(45) Date of Patent: Jul. 13, 2021

(54) MEDICAL SAFETY CONTROL APPARATUS, MEDICAL SAFETY CONTROL METHOD, AND MEDICAL SUPPORT SYSTEM

(71) Applicant: SONY CORPORATION, Tokyo (JP)

(72) Inventors: Wataru Kokubo, Tokyo (JP); Takeshi Maeda, Tokyo (JP); Tatsumi Sakaguchi, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 466 days.

(21) Appl. No.: 16/063,550

(22) PCT Filed: Dec. 2, 2016

(86) PCT No.: PCT/JP2016/085891
§ 371 (c)(1),
(2) Date: Jun. 18, 2018

(87) PCT Pub. No.: WO2017/130567
PCT Pub. Date: Aug. 3, 2017

(65) Prior Publication Data
US 2019/0000585 A1 Jan. 3, 2019

(30) Foreign Application Priority Data
Jan. 25, 2016 (JP) .............................. JP2016-011348

(51) Int. Cl.
*A61B 34/30* (2016.01)
*A61B 90/50* (2016.01)
(Continued)

(52) U.S. Cl.
CPC .......... *A61B 90/03* (2016.02); *A61B 1/00006* (2013.01); *A61B 1/00009* (2013.01);
(Continued)

(58) Field of Classification Search
CPC combination set(s) only.
See application file for complete search history.

(56) References Cited

U.S. PATENT DOCUMENTS

| | | | |
|---|---|---|---|
| 2002/0120188 A1* | 8/2002 | Brock | A61B 34/30 600/407 |
| 2004/0115606 A1* | 6/2004 | Davies | A61B 34/30 434/258 |

(Continued)

FOREIGN PATENT DOCUMENTS

| | | |
|---|---|---|
| JP | 5-211990 A | 8/1993 |
| JP | 9-66056 A | 3/1997 |

(Continued)

OTHER PUBLICATIONS

International Search Report dated Feb. 14, 2017 in PCT/JP2016/085891, 2 pages.

*Primary Examiner* — John P Leubecker
*Assistant Examiner* — Shankar Raj Ghimire
(74) *Attorney, Agent, or Firm* — Xsensus LLP

(57) ABSTRACT

A medical safety control apparatus that includes processing circuitry that obtains a surgical instrument-biological tissue distance, determine whether the surgical instrument-biological tissue distance is greater than a predetermined first restricted distance, in response to determining that the surgical instrument-biological tissue distance is not greater than the predetermined first restricted distance, issues an instruction for stopping a motion of an arm of a support arm apparatus that supports the surgical instrument, in response to determining that the surgical instrument-biological tissue distance is greater than the predetermined first restricted distance, determines whether the surgical instrument-biological tissue distance is greater than a predetermined second restricted distance, and in response to determining that the surgical instrument-biological tissue distance is not (Continued)

greater than the predetermined second restricted distance, issues a first instruction for restricting a motion speed of the arm.

14 Claims, 15 Drawing Sheets

(51) Int. Cl.
    *A61B 17/00*     (2006.01)
    *A61B 90/00*     (2016.01)
    *A61B 1/00*     (2006.01)
    *A61B 34/10*     (2016.01)
    *A61B 34/20*     (2016.01)
    *B25J 9/00*     (2006.01)

(52) U.S. Cl.
    CPC ...... *A61B 1/00039* (2013.01); *A61B 1/00055* (2013.01); *A61B 1/00149* (2013.01); *A61B 1/00193* (2013.01); *A61B 34/10* (2016.02); *A61B 34/30* (2016.02); *A61B 90/50* (2016.02); *A61B 17/00234* (2013.01); *A61B 2034/2051* (2016.02); *A61B 2034/2063* (2016.02); *A61B 2090/033* (2016.02); *A61B 2090/061* (2016.02); *A61B 2090/065* (2016.02); *B25J 9/0009* (2013.01)

(56) References Cited

U.S. PATENT DOCUMENTS

| | | | | |
|---|---|---|---|---|
| 2005/0193451 A1* | 9/2005 | Quistgaard | .......... | A61B 5/6843 414/1 |
| 2007/0144298 A1* | 6/2007 | Miller | .................... | A61B 34/25 74/490.01 |
| 2007/0151390 A1* | 7/2007 | Blumenkranz | ...... | B25J 15/0009 74/490.06 |
| 2008/0065109 A1* | 3/2008 | Larkin | .................. | A61B 1/018 606/130 |
| 2009/0192522 A1* | 7/2009 | Blumenkranz | ........ | A61B 34/37 606/130 |
| 2011/0015569 A1* | 1/2011 | Kirschenman | ..... | A61B 17/2909 604/95.01 |
| 2012/0059378 A1* | 3/2012 | Farrell | .................... | A61B 90/25 606/80 |
| 2012/0158011 A1* | 6/2012 | Sandhu | .................. | A61B 34/30 606/130 |
| 2015/0100066 A1* | 4/2015 | Kostrzewski | .......... | A61B 34/20 606/130 |
| 2015/0366546 A1* | 12/2015 | Kamen | .................. | A61B 90/11 600/461 |
| 2015/0366624 A1* | 12/2015 | Kostrzewski | .......... | A61B 34/30 606/130 |
| 2016/0000307 A1* | 1/2016 | Akimoto | ................ | A61B 1/307 600/109 |
| 2016/0100898 A1* | 4/2016 | Jinno | ..................... | A61B 17/29 606/130 |
| 2016/0158938 A1* | 6/2016 | Gombert | ................ | B25J 9/1697 700/259 |
| 2017/0212723 A1* | 7/2017 | Atarot | ..................... | G10L 15/28 |
| 2017/0360512 A1* | 12/2017 | Couture | ............ | A61B 17/1675 |
| 2018/0200006 A1* | 7/2018 | Kamikawa | ................ | B25J 9/06 |

FOREIGN PATENT DOCUMENTS

| | | | | |
|---|---|---|---|---|
| JP | 2004-223128 | A | 8/2004 | |
| JP | 2006-136385 | A | 6/2006 | |
| JP | 2007-7041 | A | 1/2007 | |
| JP | 2007-29232 | A | 2/2007 | |
| JP | 2010-104426 | A | 5/2010 | |
| JP | 2011-212245 | A | 10/2011 | |
| JP | 2013-192773 | A | 9/2013 | |
| JP | 2014-161537 | A | 9/2014 | |
| JP | 2014-223293 | A | 12/2014 | |
| JP | 2015-531271 | A | 11/2015 | |
| WO | WO-2012131660 | A1 * | 10/2012 | ............ A61B 34/76 |
| WO | WO-2014199413 | A1 * | 12/2014 | ............ A61B 34/37 |
| WO | 2015/046081 | A | 4/2015 | |

\* cited by examiner

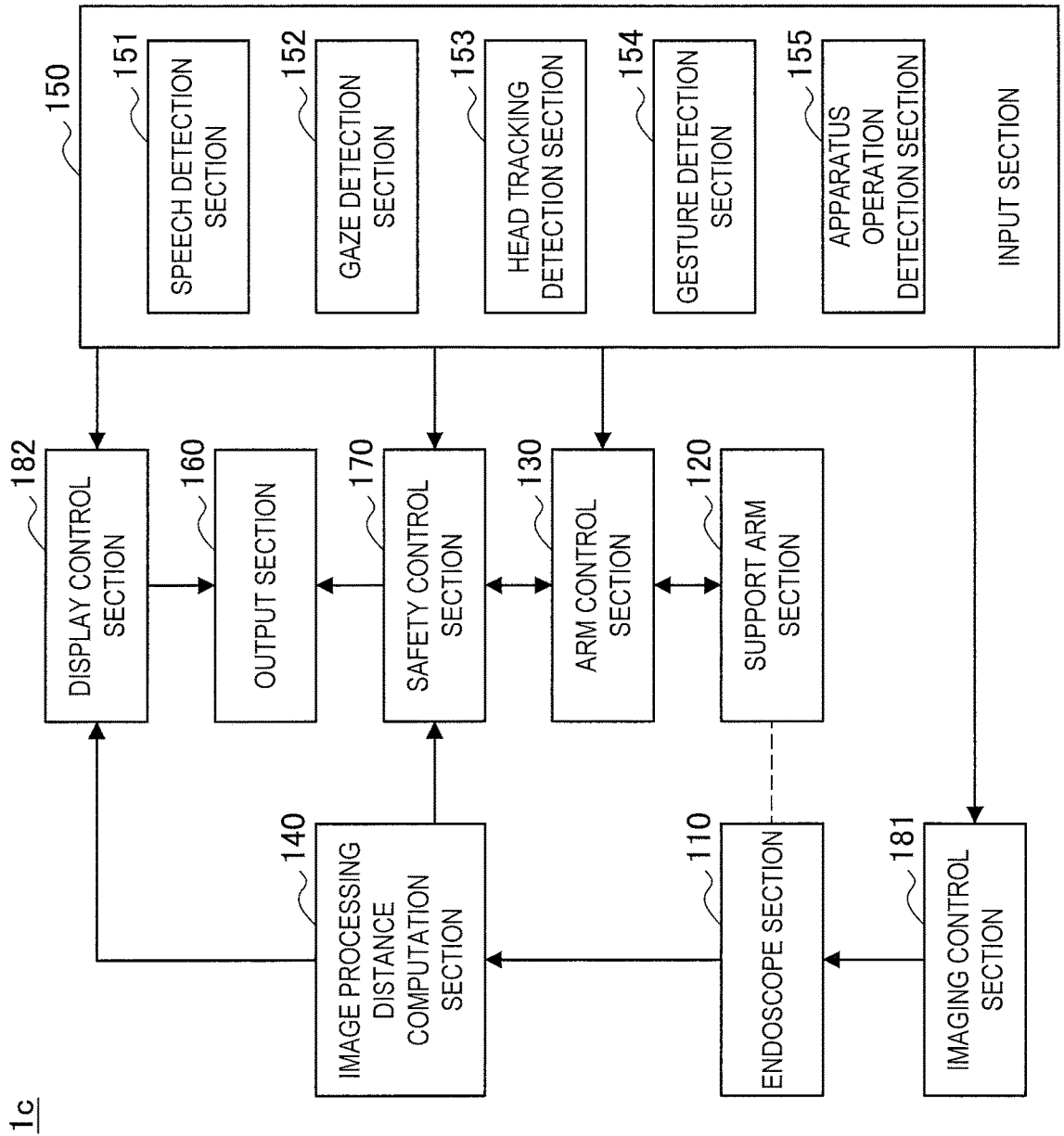

MEDICAL SAFETY CONTROL APPARATUS, MEDICAL SAFETY CONTROL METHOD, AND MEDICAL SUPPORT SYSTEM

TECHNICAL FIELD

The present disclosure relates to a medical safety control apparatus, medical safety control method, and a medical support system.

BACKGROUND ART

Recently, in the medical field, support arm apparatus are being used to support examinations and surgeries. For example, a method has been proposed in which an observation instrument for enlarged observation of an operating site, such as an endoscope or an electronic imaging microscope (video microscope) is supported by an arm section of a support arm apparatus, and a doctor carries out an examination or surgery while watching a picture captured by the observation instrument. Alternatively, there is also proposed a method in which a treatment tool such as forceps or a retractor is provided on the front end of the arm section, and the support arm apparatus is made to support or perform operations with the treatment tool which have been performed manually in the past.

Also, a surgical support system targeting such surgeries using a support arm apparatus is being developed. For example, Patent Literature 1 discloses technology in which, when supporting a surgical instrument (the observation instrument or treatment tool described above) with a manipulator, and performing surgery by operating the manipulator, three-dimensional information of a biological tissue inside the body cavity of a patient is generated from magnetic resonance imaging (MRI) or computed tomography (CT) information acquired in advance, while in addition, the position of the surgical instrument during the surgery is detected, and an image of the biological tissue generated from the three-dimensional information and the position of the surgical instrument with respect to the biological tissue are displayed on a display apparatus. Furthermore, with the technology described in Patent Literature 1, a warning is issued in the case in which the surgical instrument departs from a region or path set in advance. In this way, with such technology, a user is able to continuously grasp the relative positional relationship between the operating site and the surgical instrument, while in addition, by issuing a warning in the case in which the surgical instrument deviates from an entry path into the body cavity, for example, the execution of surgery by the surgeon is supported.

CITATION LIST

Patent Literature

Patent Literature 1: JP 2004-223128A

DISCLOSURE OF INVENTION

Technical Problem

Herein, in the technology described in Patent Literature 1 above, three-dimensional information about the operating site is generated on the basis of MRI or CT information acquired before surgery. Additionally, the position of the biological tissue during surgery is specified on the basis of the three-dimensional information generated before surgery. However, during surgery, the position and shape of the biological tissue of the patient may change over time. Consequently, in some cases, the status of the biological tissue inside the body cavity during actual surgery does not necessarily match the three-dimensional information about the biological tissue based on information acquired before surgery. In such cases, with the technology described in Patent Literature 1, the warning does not work effectively, and there is a risk of being unable to ensure safety adequately.

Also, with the technology described in Patent Literature 1, a warning is issued in the case in which the surgical instrument departs from a region or path set in advance. In other words, it is only when the surgical instrument has already departed from a safe region or path that the user realizes that one's own operation may have been mistaken, or in other words, that there is a situation in which danger may occur. However, to ensure safety more reliably, it is desirable for the user to be able to grasp the situation sooner in the case in which danger is predicted to occur.

In this way, there is conceivable room for further improvement from the perspective of safety in the technologies for ensuring the safety of a medical procedure that have been proposed so far. Accordingly, the present disclosure provides a novel and improved medical safety control apparatus, a medical safety control method, and a medical support system capable of further increasing the safety of a medical procedure.

Solution to Problem

According to the present disclosure, there is provided a medical safety control apparatus. The medical safety control apparatus issues a motion-restricting instruction for restricting a motion of an arm section of a support arm apparatus that supports a surgical instrument, on a basis of a surgical instrument-biological tissue distance, which is a distance between the surgical instrument and a biological tissue of a patient, the surgical instrument-biological tissue distance being detected while a treatment is being performed on the biological tissue by the surgical instrument.

In addition, according to the present disclosure, there is provided a medical safety control method including: issuing a motion-restricting instruction for restricting a motion of an arm section of a support arm apparatus that supports a surgical instrument, on a basis of a surgical instrument-biological tissue distance, which is a distance between the surgical instrument and a biological tissue of a patient, the surgical instrument-biological tissue distance being detected while a treatment is being performed on the biological tissue by the surgical instrument.

In addition, according to the present disclosure, there is provided a medical support system including: a support arm section that supports a surgical instrument with an arm section; an arm control section that controls a driving of the support arm section; and a medical safety control section that issues, to the arm control section, a motion-restricting instruction for restricting a motion of the arm section, on a basis of a surgical instrument-biological tissue distance, which is a distance between the surgical instrument and a biological tissue of a patient, the surgical instrument-biological tissue distance being detected while a treatment is being performed on the biological tissue by the surgical instrument.

According to the present disclosure, while a treatment is being performed on a biological tissue of a patient by a surgical instrument, the surgical instrument-biological tissue distance, which is the distance between the surgical instrument and the biological tissue, is detected. Additionally, on the basis of the detected surgical instrument-biological tissue distance, a motion-restricting instruction for restricting the motion of the arm section of the support arm apparatus that supports the surgical instrument is issued. In this way, by using the surgical instrument-biological tissue distance detected in what is called real time, the motion-restricting instruction is issued with respect to the arm section that supports the surgical instrument according to the most recent positional relationship between the surgical instrument and the biological, and thus the safety of the medical procedure can be increased further.

Advantageous Effects of Invention

According to the present disclosure as described above, it becomes possible to increase the safety of a medical procedure further. Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 16 is a block diagram illustrating an example of a functional configuration of a support system configured to allow operation input with respect to other configurations of an endoscopic surgery system through an NUI.

MODE(S) FOR CARRYING OUT THE INVENTION

Figure 1:
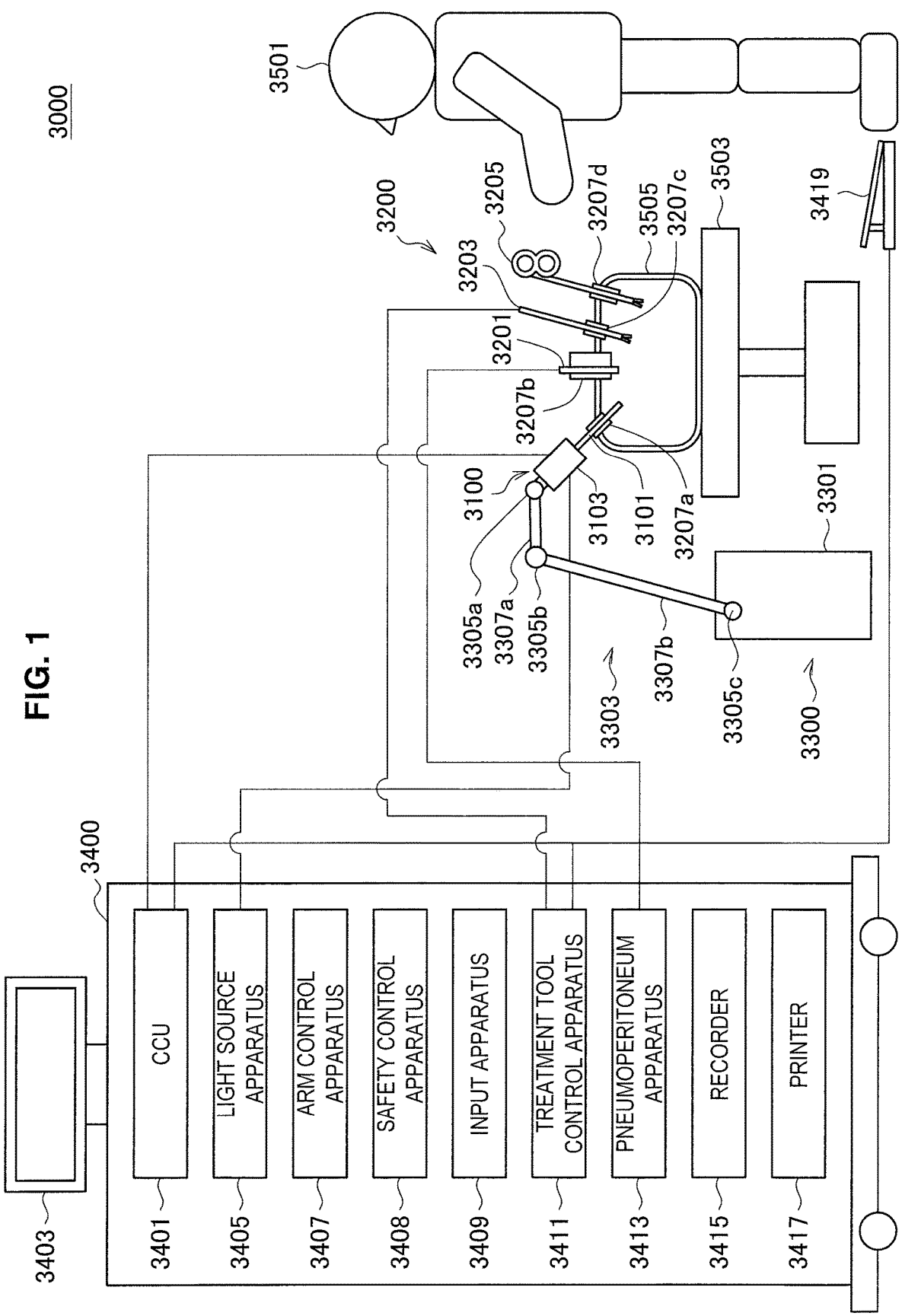
FIG. 1 is a diagram illustrating an exemplary configuration of an endoscopic surgery system according to the present embodiment.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Hereinafter, the description will proceed in the following order.

1. Configuration of endoscopic surgery system
2. Configuration of support system
3. Motion-restricting information input methods
4. Safety control method
5. Modifications
5-1. Distance measurement method
5-1-1. Case in which distance measurement sensor is provided on front end of lens tube
5-1-2. Case in which distance detection section is provided externally
5-2. Retracting motion
5-3. Operation of other configuration through NUI
5-4. Application to support arm apparatus of master-slave method
5-5. Utilization of 3D model
6. Supplement Note that the following describes a preferred embodiment of the present disclosure by taking, as an example, a case in which the present technology is applied to an endoscopic surgery system. However, the present technology is not limited to such an example, and is also applicable to medical procedures (such as various types of examinations and surgeries) performed with a surgical instrument (observation instrument and/or treatment tool) supported by a support arm apparatus. Also, in the following description, "user" is assumed to mean at least one member of the medical staff (such as a surgeon who performs surgery, a scopist who operates the endoscope, and an assistant) who use the endoscopic surgery system. The user will be described as the surgeon, the scopist, or the like only in cases where it is necessary to distinguish the user in particular.

(1. Configuration of Endoscopic Surgery System)

FIG. 1 will be referenced to describe a configuration of an endoscopic surgery system to which the support system according to the present embodiment may be applied. FIG. 1 is a diagram illustrating an exemplary configuration of an endoscopic surgery system according to the present embodiment.

FIG. 1 illustrates a situation in which a surgeon (doctor) 3501 is using an endoscopic surgery system 3000 to perform surgery on a patient 3505 lying on a patient bed 3503. As illustrated in the diagram, the endoscopic surgery system 3000 includes an endoscope 3100, other surgical instruments 3200, a support arm apparatus 3300 that supports the endoscope 3100, and a cart 3400 on which various apparatus for endoscopic surgery are provided. By applying the support system according to the present embodiment to the endoscopic surgery system 3000, safer surgery may be realized.

In endoscopic surgery, instead of opening up the abdomen by cutting the abdominal wall, tubular hole-opening tools called trocars 3207a to 3207d are used to puncture the abdominal wall in multiple places. Subsequently, the lens tube 3101 of the endoscope 3100 and other surgical instruments 3200 are inserted into the body cavity of the patient 3505 from the trocars 3207a to 3207d. In the illustrated example, a pneumoperitoneum tube 3201, an energy treatment tool 3203, and forceps 3205 are inserted into the body cavity of the patient 3505 as the other surgical instruments 3200. The energy treatment tool 3203 is a treatment tool that makes incisions into and ablates tissues, or seals blood vessels or the like, with a high-frequency electric current or ultrasonic vibration. However, the surgical instruments 3200 illustrated in the diagram are merely an example, and any of various types of surgical instruments typically used in endoscopic surgery, such as tweezers and retractors, for example, may also be used as the surgical instruments 3200.

An image of the operating site inside the body cavity of the patient 3505 taken by the endoscope 3100 is displayed on a display apparatus 3403 described later. The surgeon 3501 uses the energy treatment tool 3203 and the forceps 3205 to perform treatments, such as excising an affected area, for example, while watching in real time the image of the operating site displayed on the display apparatus 3403.

Note that, although omitted from the diagram, the pneumoperitoneum tube 3201, the energy treatment tool 3203, and the forceps 3205 are supported by a person such as the surgeon 3501 or an assistant during surgery. Alternatively, although only one support arm apparatus 3300 that supports the endoscope 3100 is provided in the example illustrated in the diagram, multiple support arm apparatus 3300 may also be provided, and the pneumoperitoneum tube 3201, the energy treatment tool 3203, and the forceps 3205 may be supported by each of the multiple support arm apparatus 3300.

(Support Arm Apparatus)

The support arm apparatus 3300 is provided with an arm section 3303 that extends from a base section 3301. In the illustrated example, the arm section 3303 includes joint sections 3305a, 3305b, and 3305c, as well as links 3307a and 3307b, and is driven by control from an arm control apparatus 3407. The endoscope 3100 is supported by the arm section 3303, with the position and attitude controlled thereby. With this arrangement, locking of the endoscope 3100 in a stable position may be realized.

However, in FIG. 1, for the sake of simplicity, the configuration of the arm section 3303 is illustrated in a simplified manner. In actuality, the shapes, numbers, and arrangement of the joint sections 3305a to 3305c and the links 3307a and 3307b, the directions of the rotation axes of the joint sections 3305a to 3305c, and the like may be set appropriately so that the arm section 3303 has the desired degrees of freedom. For example, the arm section 3303 preferably may be configured to have six or more degrees of freedom. With this arrangement, it is possible to move the endoscope 3100 freely within the movable range of the arm section 3303, and thus it becomes possible to insert the lens tube 3101 of the endoscope 3100 into the body cavity of the patient 3505 from a desired direction.

The joint sections 3305a to 3305c are provided with actuators, and the joint sections 3305a to 3305c are configured to be rotatable about a certain rotation axis in accordance with the driving of the actuators. By controlling the driving of the actuators with the arm control apparatus 3407 described later, the rotational angle of each of the joint sections 3305a to 3305c is controlled, and the driving of the arm section 3303 is controlled. With this arrangement, the position and the attitude of the endoscope 3100 are controlled.

Specifically, the actuators provided in the joint sections 3305a to 3305c are provided with various types of sensor for detecting the state of each joint section, such as encoders that detect the rotational angle of each joint section, and torque sensors that detect the torque acting on each joint section. The detection values of these sensors are transmitted to the arm control apparatus 3407. The arm control apparatus 3407 includes an internal model in which the geometric state and the mechanical state of the arm section 3303 are expressed by internal coordinates of the support arm apparatus 3300, and on the basis of the internal model and detection values from the sensors, the arm control apparatus 3407 is able to grasp the current state of the joint sections 3305a to 3305c, that is, the current state (such as the position, attitude, and speed) of arm section 3303. The arm control apparatus 3407 computes, on the basis of the grasped state of the arm section 3303, drive control quantities (for example, the rotational angle and the driving torque) of each joint section corresponding to operation input with respect to the motion of the arm section 3303 from the user, and drives each joint section in accordance with the drive control quantities.

In the present embodiment, the arm control apparatus 3407 controls the driving of the arm section 3303 by force control. In the case in which force control is applied, the arm control apparatus 3407, in response to an operation performed by the doctor (scopist) who operates the endoscope 3100 directly touching the arm section 3303 or the endoscope 3100 (hereinafter also designated a direct operation), is able to execute what is called power assist control, in which the actuators of each of the joint sections 3305a to 3305c are driven so that the arm section 3303 moves smoothly following the external force from the direct operation. With this arrangement, when the scopist moves the arm section 3303 while touching the arm section 3303 directly, the arm section 3303 can be moved with comparatively light force. Consequently, it becomes possible to move the endoscope 3100 more intuitively with a simpler operation, and convenience for the scopist can be improved.

However, the present embodiment is not limited to such an example, and the arm control apparatus 3407 may also control the driving of the arm section 3303 by position control. Additionally, the arm section 3303 may also be operated according to another method other than a direct operation. For example, by having the user perform appropriate operation input via an input apparatus 3409 (including a footswitch 3419), the driving of the arm section 3303 may be controlled appropriately by the arm control apparatus 3407 in accordance with the operation input, and the position and the attitude of the endoscope 3100 may be controlled. Alternatively, the arm section 3303 may be operated by a user gesture or the like. Alternatively, the arm section 3303 may be operated by what is called a master-slave method. In this case, the arm section 3303 may be operated remotely by a user via the input apparatus 3409 installed in a location distanced from the operating room. Such driving of the arm section 3303 according to operations other than the direct operation will be described further in (5-3. Operation of other configuration through NUI) and (5-4. Application to support arm apparatus of master-slave method) below.

(Endoscope)

The endoscope 3100 includes a lens tube 3101 having a region of certain length from the front end that is inserted into the body cavity of the patient 3505, and a camera head 3103 connected to the base end of the lens tube 3101. The endoscope 3100 is what is called a rigid scope having a rigid lens tube 3101. However, the present embodiment is not limited to such an example, and the endoscope 3100 may also be configured as what is called a flexible scope having a flexible lens tube 3101.

On the front end of the lens tube 3101, there is provided an opening into which an objective lens is fitted. The endoscope 3100 is configured as a forward-viewing scope in which the objective lens is disposed so that the extension direction of the lens tube 3101 and the optical axis are approximately aligned. A light source apparatus 3405 described later is connected to the endoscope 3100. Light generated by the light source apparatus 3405 is guided up to the front end of the lens tube by a light guide extending inside the lens tube 3101, and is radiated through the objective lens towards an observation target inside the body cavity of the patient 3505. Note that the present embodiment is not limited to such an example, and the endoscope 3100 may also be an oblique-viewing scope or a side-viewing scope.

An optical system and an image sensor are provided inside the camera head 3103, and reflected light (observation light) from the observation target is condensed onto the image sensor by the optical system. Observation light is photoelectrically converted by the image sensor, and an electrical signal corresponding to the observation light, or in other words, an image signal corresponding to the observed image, is generated. The image signal is transmitted as RAW data to a camera control unit (CCU) 3401 described later. Note that the camera head 3103 may be provided with a function of adjusting the magnification and the focal length by appropriately driving the optical system.

Note that in the present embodiment, to support stereoscopic vision (3D display) or the like, multiple image sensors are provided in the camera head 3103. In other words, the endoscope 3100 may be configured as a stereo camera. In this case, multiple relay optical subsystems are provided inside the lens tube 3101 to guide the observation light to each of the multiple image sensors. However, the present embodiment is not limited to such an example, and the endoscope 3100 may also be configured so that the camera head 3103 includes a single image sensor.

(Various Apparatus Provided on Cart)

The CCU 3401 includes a processor such as a central processing unit (CPU) or a graphics processing unit (GPU), and centrally controls the operation of the endoscope 3100 and the display apparatus 3403. Specifically, the CCU 3401 subjects an image signal received from the camera head 3103 to various types of image processing for displaying an image based on the image signal, such as a development process (demosaicing process), for example. The CCU 3401 provides an image signal that has been subjected to such image processing to the display apparatus 3403. Also, the CCU 3401 transmits a control signal to the camera head 3103 to control the driving thereof. The control signal may include information related to imaging conditions, such as the magnification and the focal length.

The display apparatus 3403, under control by the CCU 3401, displays an image based on an image signal subjected to image processing by the CCU 3401. In a case in which the endoscope 3100 supports imaging at a high resolution such as 4K or 8K, and/or supports 3D display, for example, an apparatus compatible with each and capable of high-resolution display and/or capable of 3D display may be used as the display apparatus 3403. Also, the display apparatus 3403, in accordance with an instruction from a safety control apparatus 3408 described later, displays a warning regarding the operation of the endoscope 3100 by the scopist, in a format such as text, for example.

The light source apparatus 3405 includes a light source such as a light-emitting diode (LED), for example, and supplies the endoscope 3100 with irradiating light when imaging the operating site.

The arm control apparatus 3407 includes a processor such as a CPU, for example, and by operating in accordance with a predetermined program, controls the driving of the arm section 3303 of the support arm apparatus 3300 in accordance with a predetermined control method. Note that since any of various known types of methods can be applied as the specific method by which the arm control apparatus 3407 controls the driving of the arm section 3303, a detailed description thereof is omitted herein.

The safety control apparatus 3408 includes a processor such as a CPU, for example, and cooperates with the CCU 3401 and the arm control apparatus 3407 to execute various types of controls for supporting operations by the scopist in surgeries using the endoscopic surgery system 3000, with the objective of ensuring safety. Details regarding the functions of the safety control apparatus 3408 will be described further in (2. Configuration of support system) below.

The input apparatus 3409 is an input interface with respect to the endoscopic surgery system 3000. Through the input apparatus 3409, the user is able to input various information and instructions into the endoscopic surgery system 3000. For example, through the input apparatus 3409, the user inputs various information related to surgery, such as physical information about the patient, and information about surgical procedures. As another example, through the input apparatus 3409, the user inputs instructions to drive the arm section 3303, instructions to change the imaging conditions of imaging by the endoscope 3100 (such as the type of irradiating light, the magnification, and the focal length), and the like. Also, through the input apparatus 3409, the user is able to input various types of information (such as the motion-restricting information described later) processed in the support system.

The type of the input apparatus 3409 is not limited, and the input apparatus 3409 may be any of various known types of input apparatus. For example, a mouse, a keyboard, a touch panel, a switch, the footswitch 3419, and/or a lever and the like may be applied as the input apparatus 3409. In the case in which a touch panel is used as the input apparatus 3409, the touch panel may be provided on the display screen of the display apparatus 3403.

Alternatively, the input apparatus 3409 may be a device worn by the user, such as an eyeglasses-style wearable device or a head-mounted display (HMD), for example, and various types of input may be performed in accordance with the user's gestures or gaze motions, head tracking, or the like detected by these devices. Alternatively, the input apparatus 3409 may be a camera capable of detecting motions of the user. Various types of input may be performed in accordance with the user's gestures or gaze detected from a picture imaged by the camera. Alternatively, the input apparatus 3409 may be a microphone capable of picking up the user's speech. Various types of input may be performed by speech through the microphone. In this way, by configuring the input apparatus 3409 to be capable of accepting the input of various types of information in a non-contact manner, a user belonging to a clean area in particular (for example, the surgeon 3501) becomes able to operate equipment belonging to an unclean area in a non-contact manner. Also, since the user becomes able to operate equipment without taking one's hands away from the tools the user is holding, user convenience is improved.

A treatment tool control apparatus 3411 controls the driving of the energy treatment tool 3203 to cauterize or make incisions into tissue, seal blood vessels, or the like. A pneumoperitoneum apparatus 3413 delivers gas into the body cavity through the pneumoperitoneum tube 3201 to inflate the body cavity of the patient 3505 for the purpose of securing a field of view for the endoscope 3100 and securing a workspace for the surgeon 3501. A recorder 3415 is an apparatus capable of recording various types of information related to surgery. A printer 3417 is an apparatus capable of printing out various types of information related to surgery in various formats, such as text, images, or graphs.

The above describes the configuration of the endoscopic surgery system 3000.

(2. Configuration of Support System)

Figure 2:
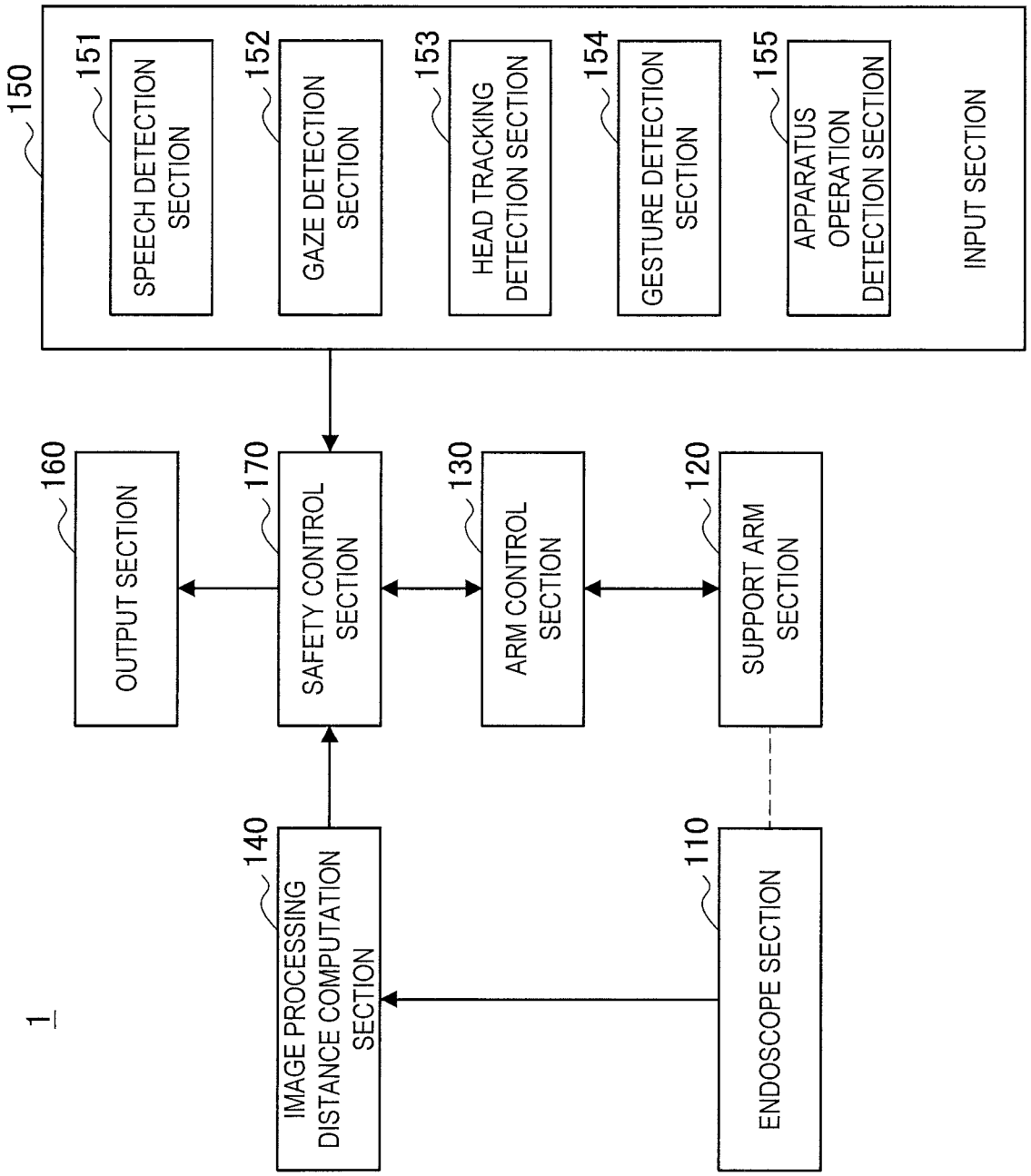
FIG. 2 is a block diagram illustrating an example of a functional configuration of a support system according to the present embodiment.

FIG. 2 will be referenced to describe a configuration of the support system according to the present embodiment, which is applied to the endoscopic surgery system 3000 described above. FIG. 2 is a block diagram illustrating an example of a functional configuration of the support system according to the present embodiment. Note that the support system according to the present embodiment supports the user who operates surgical instruments supported by the support arm apparatus through the support arm apparatus during examinations and surgeries. The present embodiment is described by taking as an example a case in which, when the scopist operates the endoscope while moving the arm section of the support arm apparatus by a direct operation, the support system supports the operations of the scopist. However, the present embodiment is not limited to such an example, and in the case in which another surgical instrument supported by the support arm apparatus is operated by another user, the support system may also support the operation of the other surgical instrument by the other user.

Referring to FIG. 2, the support system 1 according to the present embodiment is provided with an endoscope section 110, a support arm section 120, an arm control section 130, an image processing distance computation section 140, an input section 150, an output section 160, and a safety control section 170 as functions thereof.

The functions of the endoscope section 110 may be realized by the endoscope 3100 illustrated in FIG. 1. The endoscope section 110 captures an image of the operating site inside the body cavity of a patient. The endoscope section 110 provides information about the captured image of the operating site of the patient to the image processing distance computation section 140.

The functions of the support arm section 120 may be realized by the support arm apparatus 3300 illustrated in FIG. 1. The support arm section 120 supports the endoscope section 110 by the arm section, and in addition, controls the position, attitude, and motion of the endoscope section 110 by driving the arm section under control from the arm control section 130. From the support arm section 120, information indicating the state of each joint section acquired by various sensors (such as encoders and torque sensors) provided in each joint section of the arm section is provided to the arm control section 130. Note that in FIG. 2, to indicate that the endoscope section 110 is being supported by the arm section of the support arm section 120, the two sections are joined by a dashed line.

The functions of the arm control section 130 may be realized by the arm control apparatus 3407 illustrated in FIG. 1. The arm control section 130 controls the position, attitude, and motion of the endoscope section 110 by controlling the driving of the arm section in the support arm section 120 in response to information indicating the state of each joint section provided from the support arm section 120, and operation input by the scopist. At this time, in the present embodiment, the arm control section 130 receives an instruction (hereinafter also called a motion-restricting instruction) for restricting the motion of the support arm section 120 from the safety control section 170, and drives the arm section with a restriction set in accordance with the motion-restricting instruction. Details regarding the motion-restricting instruction by the safety control section 170 will be described later.

The image processing distance computation section 140 computes, on the basis of an image of the operating site provided from the endoscope section 110, the distance (herein called the lens tube-biological tissue distance) between the front end of the lens tube of the endoscope, and an object included in the image (biological tissue inside the body cavity of the patient). In the exemplary configuration illustrated in the diagram, since the endoscope section 110 is configured as a stereo camera, and since the captured image is acquired as an image including three-dimensional information, the image processing distance computation section 140 is able to compute the lens tube-biological tissue distance by performing various types of image processing on the image signal acquired in the endoscope section 110, and also by executing a distance computation process. Note that since any of various known types of methods may be used as the specific method of computing the distance using a stereo camera, a detailed description is omitted herein.

In the present embodiment, the image processing distance computation section 140 computes the lens tube-biological tissue distance in real time during surgery. Herein, in this specification, "during surgery" means at least the period during which a treatment is being performed on the biological tissue of the patient by a surgical instrument. For example, in the case of treating the operations of the scopist in the endoscopic surgery system 3000 as the target of support like in the embodiment presently being described, "during surgery" means at least the period during which the operating site is being imaged by the endoscope section 110. Also, in this specification, "executed in real time" means at least being executed at least one time during surgery. In the present embodiment, for example, for every frame rate of imaging by the endoscope section 110, the image processing distance computation section 140 computes the lens tube-biological tissue distance on the basis of the image signal acquired for each frame rate. However, the computation interval of the lens tube-biological tissue distance by the image processing distance computation section 140 is not limited to such an example, and the image processing distance computation section 140 may also compute the lens tube-biological tissue distance on a wider time interval. The computation interval may be decided appropriately so that safety through motion restriction of the support arm section 120 according to the lens tube-biological tissue distance described later is secured adequately.

The image processing distance computation section 140 provides information about the computed lens tube-biological tissue distance to the safety control section 170 continuously every time the lens tube-biological tissue distance is computed.

Note that the functions of the image processing distance computation section 140 may be realized by the cooperation of the CCU 3401 and the safety control apparatus 3408. In this case, for example, the image processing is executed by the CCU 3401, and computational processing related to the distance computation is executed by the safety control apparatus 3408. Alternatively, the functions of the image processing distance computation section 140 may also be realized by either one of the cooperation of the CCU 3401 and the safety control apparatus 3408.

The functions of the input section 150 may be realized by the input apparatus 3409 illustrated in FIG. 1. The input section 150 receives information (hereinafter also called motion-restricting information) about the motion restriction of the support arm section 120 by the user. Specifically, the motion-restricting information includes information about various conditions that prescribe the motion restriction, for example, information regarding whether or not to execute motion restriction, a first restricted distance and a second restricted distance, an advancement region and a peripheral region, an allowed speed when restricting the motion speed, and the like to be described later.

In the present embodiment, the input section 150 may support a wide variety of input methods. In the exemplary configuration illustrated in the diagram, the input section 150 additionally includes a speech detection section 151, a gaze detection section 152, a head tracking detection section 153, a gesture detection section 154, and an apparatus operation detection section 155 as functions thereof. The user is able to input the motion-restricting information by utilizing any of these functions.

The speech detection section 151 is realized by a sound pickup apparatus such as a microphone, for example, and detects the user's speech. The gaze detection section 152 is realized by a gaze detection sensor provided in an HMD or an eyeglasses-style wearable device, for example, and detects the movement of the user's gaze. The head tracking detection section 153 is realized by an acceleration sensor provided in a device worn on the user's head, such as an HMD or an eyeglasses-style wearable device, for example, and detects the movement of the user's head. The gesture detection section 154 is realized by a camera apparatus capable of imaging the user provided inside the operating room, for example, or an acceleration sensor provided in a device worn on the user's body, such as a wristwatch-style wearable device, for example, and detects gestures by the user. The apparatus operation detection section 155 is realized by any of various types of input apparatus other than the above-described (such as a footswitch, a lever, a button, or a touch sensor, for example), and detects operation input by the user through these apparatus.

Note that operation input through the speech detection section 151, the gaze detection section 152, the head tracking detection section 153, and the gesture detection section 154 described above is operation input through what is called a natural user interface (NUI), and enables operation input in a non-contact manner. On the other hand, the apparatus operation detection section 155 includes a function of accepting operation input other than NUI. Herein, in the medical field, a user belonging to a clean area may want to supply operation input to an apparatus belonging to an unclean area in some cases. In such cases, in the case in which operation input cannot be performed in a non-contact manner, since the user is unable to perform operation input while touching the input apparatus directly, the user is required to verbally instruct an assistant to perform the operation input through the input apparatus, for example, which is inefficient. In contrast, in the present embodiment, by applying the NUI, operation input in a non-contact manner becomes possible, thereby making it possible for a user belonging to a clean area to perform operation input directly, even with respect to an apparatus belonging to an unclean area. Consequently, more intuitive operation input becomes possible, and user convenience may be improved. Note that examples of a UI for inputting the motion-restricting information will be described further in (3. Motion-restricting information input methods) below.

The input section 150 provides motion-restricting information input by the user to the safety control section 170.

The functions of the output section 160 may be realized by the display apparatus 3403 illustrated in FIG. 1. Additionally, the output section 160 may also be realized by another visual output apparatus, such as an indicator lamp not illustrated in FIG. 1, or a sound output apparatus such as a speaker. The output section 160 issues a warning by display, sound, or the like with respect to an operation of the endoscope section 110 by the scopist, on the basis of an instruction from the safety control section 170. The warning may be issued by displaying text or the like with the display apparatus, emitting light from an indicator lamp, and/or outputting sound and an alarm or the like with the sound output apparatus. At this time, in the present embodiment, the warning instruction from the safety control section 170 may be set in stages. Correspondingly, the output section 160 may be configured to issue the warning in stages. For example, by appropriately controlling the font size of displayed text, the intensity and color type of emitted light from the indicator lamp, the loudness of sound, and the like, the output section 160 is able to issue each of a comparatively small-scale warning and a comparatively large-scale warning.

The functions of the safety control section 170 may be realized by the safety control apparatus 3408 illustrated in FIG. 1. The safety control section 170 issues a motion-restricting instruction to the arm control section 130 on the basis of the lens tube-biological tissue distance provided from the image processing distance computation section 140, and the motion-restricting information provided from the input section 150. Also, the safety control section 170 issues an instruction to issue the warning to the output section 160 on the basis of the lens tube-biological tissue distance and the motion-restricting information. Note that at this time, the safety control section 170 may also acquire information about the state of the arm section from the arm control section 130, and utilize the position of the lens tube of the endoscope grasped on the basis of the information to appropriately correct the lens tube-biological tissue distance provided from the image processing distance computation section 140.

Specifically, the safety control section 170 sets the first restricted distance and the second restricted distance on the basis of the motion-restricting information. Herein, the first restricted distance is set as a value close to a minimum distance (allowed boundary distance) between the lens tube and the operating site which may be allowed to ensure safety. Also, the second restricted distance is a longer distance than the first restricted distance, and is set as a distance that, although not immediately dangerous, has a risk of reaching an allowed boundary distance soon if the endoscope continues to advance farther. The safety control section 170 issues the motion-restricting instruction and the warning instruction according to the relationship between the lens tube-biological tissue distance, and the first restricted distance and second restricted distance.

However, as described above, in the present embodiment, since the lens tube-biological tissue distance is computed on the basis of a captured image from a stereo camera, the distance between each object included in the imaging range of the endoscope and the lens tube may be computed as the lens tube-biological tissue distance. In other words, a two-dimensional distribution of the lens tube-biological tissue distance in a plane approximately perpendicular to the advancement direction of the lens tube may be obtained. Utilizing the above, in the present embodiment, the safety control section 170 sets multiple regions in the advancement direction of the lens tube, and issues the motion-restricting instruction and the warning instruction according to the relationship between the lens tube-biological tissue distance, and the first restricted distance and second restricted distance, in each of the multiple regions. Note that in the following, for the sake of convenience, distance measurement capable of obtaining such a two-dimensional distribution of the lens tube-biological tissue distance is also called planar distance measurement.

Figure 3:
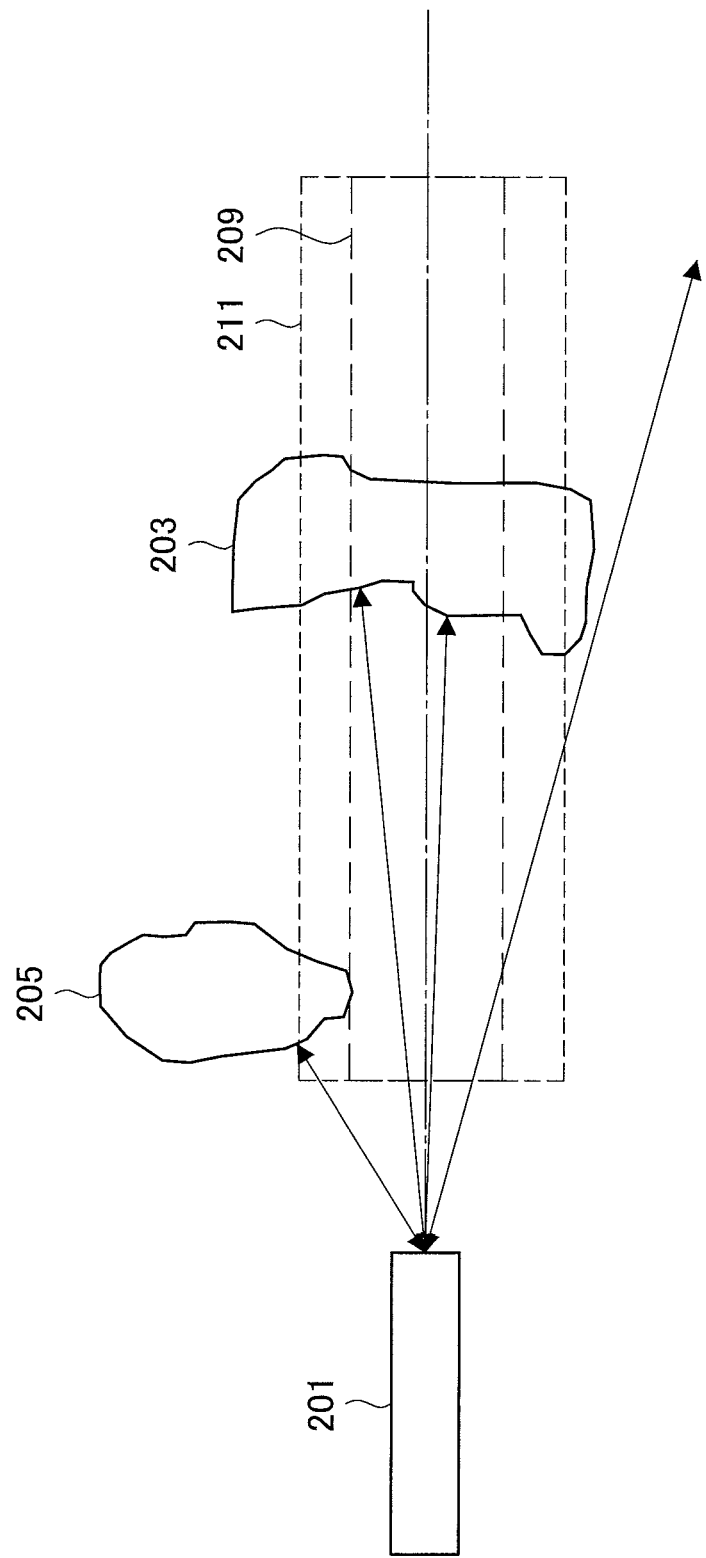
FIG. 3 is a diagram schematically illustrating a state of planar distance measurement.
Figure 4:
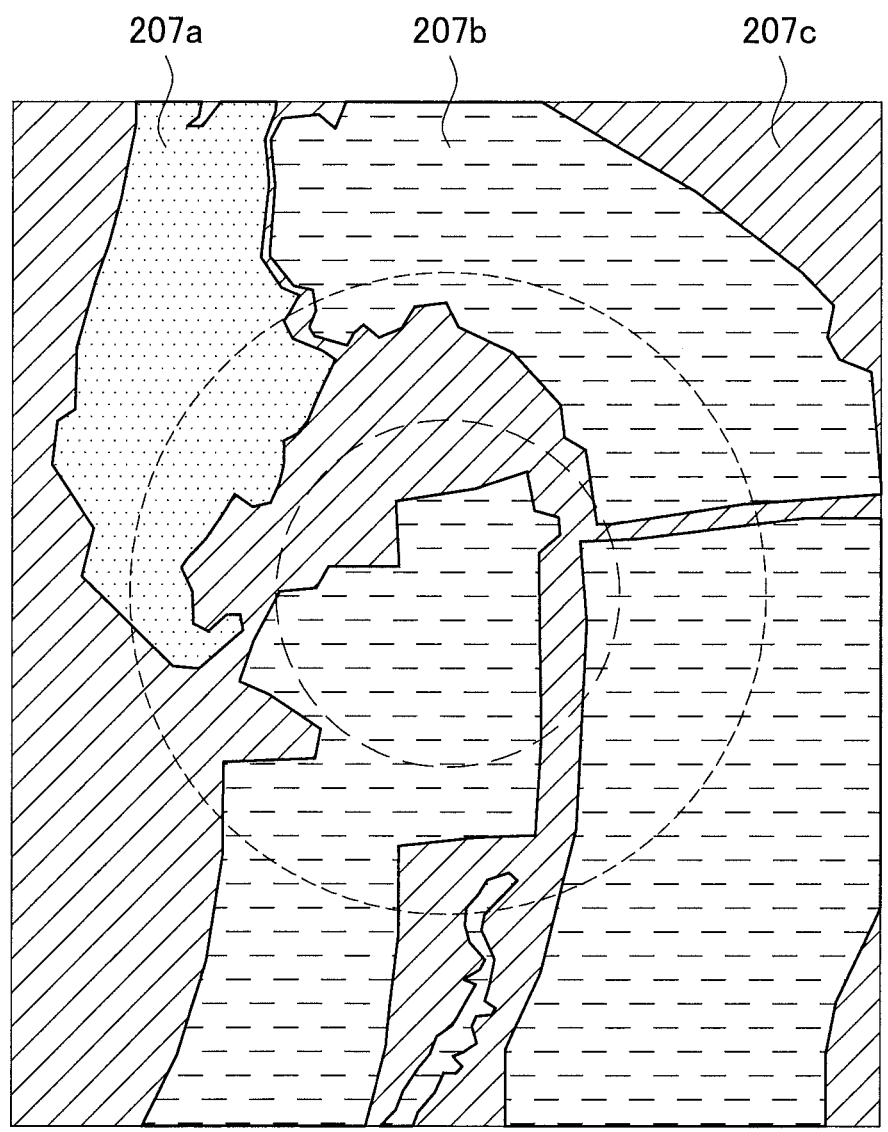
FIG. 4 is a diagram schematically illustrating a planar distance measurement result.

An example of planar distance measurement and region division will be described with reference to FIGS. 3 and 4. FIG. 3 is a diagram schematically illustrating a state of planar distance measurement. FIG. 4 is a diagram schematically illustrating a result of planar distance measurement.

As illustrated in FIG. 3, assume that inside the body cavity, a biological tissue 203 exists in front in the advancement direction of a lens tube 201, and another biological tissue 205 is positioned in the advancement direction of the lens tube 201, but is positioned in a location away from the front. However, the biological tissue 205 is positioned at a location closer to the lens tube 201 than the biological tissue 203.

In this case, if the lens tube-biological tissue distance is computed on the basis of a captured image from the stereo camera, a distribution of the lens tube-biological tissue distance inside the captured image may be obtained. FIG. 4 schematically illustrates a distribution of the lens tube-biological tissue distance inside the captured image. In the example illustrated in FIG. 4, the computed lens tube-biological tissue distance is divided into three stages, and the regions belonging to each of the distances are illustrated with different hatching applied. A short-range region 207a is a region in which the lens tube-biological tissue distance is comparatively near, a medium-range region 207b is a region in which the lens tube-biological tissue distance is moderate, and a long-range region 207c is a region in which the lens tube-biological tissue distance is comparatively far. Referring to FIG. 4, the detection of the biological tissue 205 positioned in the short-range region 207a is demonstrated.

Herein, for the sake of convenience in description, assume that the first restricted distance is set as the value of the boundary between the short-range region 207a and the medium-range region 207b, and that the second restricted distance is set as the value of the boundary between the medium-range region 207b and the long range region 207c. In this case, for example, the safety control section 170 may issue the motion-restricting instruction and the warning instruction by using the existence of the short-range region 207a and/or the medium-range region 207b inside the captured image as a judgment criterion.

However, referring to FIG. 4, the short-range region 207a is distributed in a location away from the center inside the captured image. Consequently, as also demonstrated from the positional relationship illustrated in FIG. 3, even if the lens tube 201 continues to advance in the extension direction, the danger that the lens tube 201 will collide with the biological tissue 205 positioned in the short-range region 207a is thought to be low. In such a case, if the motion-restricting instruction and the warning instruction are issued by simply using the existence of the short-range region 207a and/or the medium-range region 207b inside the captured image as a judgment criterion as above, there is an opposite risk of interfering with the operation by the scopist.

Consequently, in the present embodiment, the safety control section 170 sets multiple regions in the advancement direction of the lens tube 201, on the basis of the motion-restricting information. The multiple regions may be set as concentric regions centered on the optical axis of the lens tube 201. In the example illustrated in the drawing, an advancement region 209, which is a region into which the lens tube 201 will advance, and a peripheral region 211, which is a region in the periphery of the advancement region, are set. The advancement region 209 is set as a cylindrical region in the advancement direction of the lens tube 201, having a diameter that is slightly larger than the outer diameter of the lens tube 201. The peripheral region 211 is set as a hollow cylindrical region surrounding the periphery of the advancement region 209.

The safety control section 170 issues the motion-restricting instruction and the warning instruction according to the relationship between the lens tube-biological tissue distance, and the first restricted distance and/or second restricted distance, in each of the advancement region 209 and the peripheral region 211. Specifically, in the case in which the lens tube-biological tissue distance is less than or equal to the first restricted distance in the advancement region 209, the safety control section 170 issues the motion-restricting instruction to the arm control section 130 so as to stop the movement of the lens tube 201 in the advancement direction (that is, to stop the motion in the advancement direction of the arm section of the support arm section 120 at that time). Additionally, the safety control section 170 also issues an instruction to the output section 160 to issue a comparatively large-scale warning.

Also, in the case in which the lens tube-biological tissue distance is less than or equal to the second restricted distance in the advancement region 209, the safety control section 170 issues the motion-restricting instruction to the arm control section 130 so as to restrict the movement speed of the lens tube 201 (that is, the motion speed of the arm section of the support arm section 120). Additionally, the safety control section 170 also issues an instruction to the output section 160 to issue a comparatively small-scale warning.

In addition, in the case in which the lens tube-biological tissue distance is less than or equal to the first restricted distance in the peripheral region 211, the safety control section 170 instructs the arm control section 130 to restrict the motion speed. Additionally, the safety control section 170 also issues an instruction to the output section 160 to issue a comparatively small-scale warning.

In addition, in cases other than the above, the safety control section 170 does not issue the motion-restricting instruction and the warning instruction, and issues an instruction to the arm control section 130 to cause the arm section to execute normal motion. Herein, normal motion refers to motion in which a motion restriction is not imposed, and the arm section moves freely in accordance with operations by the scopist.

The arm control section 130 receives the instruction from the safety control section 170, and drives the support arm section 120 with the restriction applied. At this time, the arm control section 130 drives the support arm section 120 while prioritizing the instruction from the safety control section 170 over the operation with respect to the support arm section 120 by the scopist. With this arrangement, even if the scopist makes a mistake in operation and brings the lens tube 201 unnecessarily close to the biological tissues 203 and 205, the movement speed of the lens tube 201 is lowered, or the movement of the lens tube 201 is stopped, and the safety of the patient is ensured. Also, at the same time, since a comparatively small-scale warning or large-scale warning is issued by the output section 160, the scopist is able to grasp from the warning that a problem has occurred with one's own operation. At this time, according to the present embodiment, since the lens tube-biological tissue distance is detected in real time, instructions are issued by the safety control section 170 on the basis of a more accurate positional relationship between the lens tube 201 and the biological tissues 203 and 205. Consequently, it becomes possible to further improve the safety of surgery.

Also, in the present embodiment, as above, by providing two types of restricted distances (the first restricted distance and the second restricted distance), the motion restriction of the arm section of the support arm section 120 and the warning by the output section 160 may be executed in stages, according to the lens tube-biological tissue distance. Consequently, at the stage in which the motion speed of the arm section of the support arm section 120 is restricted, and the small-scale warning is issued by the output section 160, the scopist is able to grasp that there is a possibility of danger occurring, and correct one's own operation. In this way, according to the present embodiment, since it is possible to inform the scopist of the positional relationship between the lens tube 201 and the biological tissues 203 and 205 at an earlier stage before danger actually occurs, safety may be increased further.

Also, as above, by issuing the motion-restricting instruction and the warning instruction with additional consideration for the advancement region 209 and the peripheral region 211 of the lens tube 201, more fine-grained judgment criteria regarding whether or not to execute a motion restriction and whether or not to issue a warning may be set, making it possible to execute the motion restriction and the warning in multiple stages. Consequently, unnecessary motion restrictions and warnings can be reduced, and convenience for the scopist can be improved further. Note that although two regions (the advancement region 209 and the peripheral region 211) are set in the above example, more regions may be set, and even more fine-grained judgment criteria regarding whether or not to execute a motion restriction and whether or not to issue a warning may be set according to these regions. With this arrangement, the motion restriction and the warning can be executed in even more stages, and convenience for the scopist can be improved even further.

Also, in the foregoing embodiment, the advancement region 209 and the peripheral region 211 are set as a cylindrical region and a hollow cylindrical region, respectively, but the advancement region 209 and the peripheral region 211 are not limited to such an example. The sizes and shapes of the advancement region 209 and the peripheral region 211 may be set arbitrarily. For example, the advancement region 209 and the peripheral region 211 may be set as cones (such as circular cones or triangular pyramids) whose apex is set to the front end of the lens tube 201.

Note that the advancement region 209 and the peripheral region 211 are set in space as a cylindrical region and a hollow cylindrical region, respectively, as illustrated in FIG. 3, for example, but in actuality, the safety control section 170 sets the advancement region 209 and the peripheral region 211 virtually with respect to a captured image (distance measurement image) as illustrated in FIG. 4. Consequently, when setting the advancement region 209 and the peripheral region 211, the safety control section 170 may execute appropriate correction processes and the like so that the desired advancement region 209 and peripheral region 211 are set on the basis of the configuration of the optical system of the endoscope section 110, the detected distances of biological tissues, the shapes of the advancement region 209 and the peripheral region 211, and the like.

Herein, the motion-restricting information may be input by the user through the input section 150, either before surgery or during surgery. By enabling the motion-restricting information to be input during surgery, convenience may be improved for the user, particularly the scopist who is operating the endoscope section 110. For example, during surgery, in a case in which it becomes necessary to perform what is called an irregular operation, such as a case in which it becomes necessary to bring the lens tube up close to a biological tissue, there is a risk that the motion restriction by the safety control section 170 instead may impede the operation by the scopist. In such a case, by allowing the setting regarding the motion restriction to be modified appropriately by the scopist oneself during surgery, the scopist becomes able to remove the motion restriction or shorten the first restricted distance and the second restricted distance as necessary, for example, thereby making it possible to perform operations more smoothly. Note that methods of inputting the motion-restricting information will be described further in (3. Motion-restricting information input methods) below.

Note that in the support system 1, in the safety control section 170, in accordance with a user instruction, it is possible to switch between a setting mode in which various conditions that prescribe motion restriction (such as the first restricted distance, the second restricted distance, the advancement region, and the peripheral region) are set, and an operating mode in which the arm section is operated by the user. The user switches to the setting mode, and then inputs the motion-restricting information. In the setting mode, the safety control section 170 sets various conditions that prescribe the motion restriction, on the basis of the input motion-restricting information. When the input of the motion-restricting information is finished, the user switches to the operating mode, and then operates the arm section. In the operating mode, the safety control section 170 issues the motion-restricting instruction and the warning instruction as appropriate, in accordance with the various set conditions that prescribe the motion restriction.

Herein, in the above embodiment, in the case in which the safety control section 170 issues the motion-restricting instruction to the arm control section 130 to stop the movement of the lens tube 201 in the advancement direction (that is, in the case of issuing the motion-restricting instruction to the arm control section 130 to stop the motion of the arm section), after that, if the scopist is unable to move the lens tube 201 until the motion restriction is released in the setting mode, there is a concern about impeding the progress of surgery. Consequently, in the case in which the safety control section 170 issues the motion-restricting instruction to the arm control section 130 to stop the motion of the arm section, after a predetermined time, the safety control section 170 may also issue a motion-restricting instruction to the arm control section 130 to cause the arm section to operate so that the lens tube 201 is movable while restricting the motion speed only in the direction that increases the lens tube-biological tissue distance. With this arrangement, even if the motion of the arm section is stopped by the motion restriction, soon after it becomes possible to move the lens tube 201 by an operation of the scopist if the lens tube 201 is moved in a safer direction at a safer speed, thereby making it possible to proceed with surgery smoothly.

The above describes a configuration of the support system 1 according to the present embodiment. As described above, according to the present embodiment, on the basis of the lens tube-biological tissue distance which is detected in real time, a motion-restricting instruction is issued to the support arm section 120, while in addition, a warning instruction is issued to the output section 160. Consequently, safer surgery may be realized.

Figure 5:
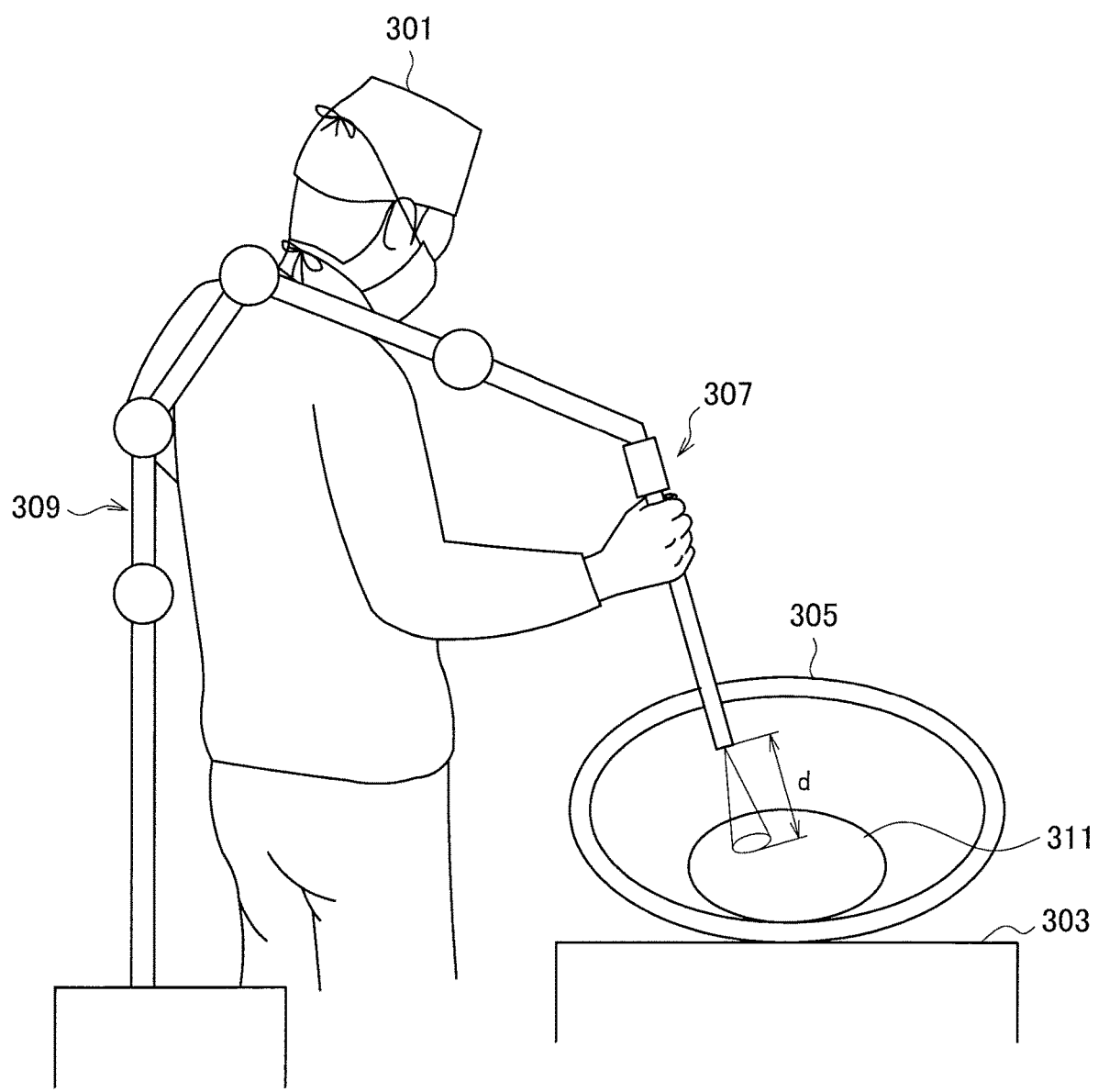
FIG. 5 is a diagram illustrating a state of surgery using the support system according to the present embodiment.

Herein, the support system 1 according to the present embodiment is particularly beneficial when the scopist operates the endoscope section 110 by a direct operation with respect to the support arm section 120. FIG. 5 will be referenced to describe the reason for the above.

FIG. 5 is a diagram illustrating a state of surgery using the support system 1 according to the present embodiment. FIG. 5 illustrates a state in which a scopist 301 has inserted the lens tube of an endoscope 307 into a patient 305 on a patient bed 303, and is operating the position and the attitude of the lens tube. The endoscope 307 is supported by a support arm apparatus 309, and the scopist 301 is able to operate the endoscope 307 by a direct operation with respect to the support arm apparatus 309. The endoscope 307 and the support arm apparatus 309 may form the endoscope section 110 and the support arm section 120 in FIG. 2.

According to the support system 1, the lens tube-biological tissue distance d, namely, the distance between the front end of the lens tube of the endoscope section 110 and a biological tissue 311 inside the body cavity of the patient 305, is detected in real time. Additionally, on the basis of the detected lens tube-biological tissue distance d, the motion of the support arm apparatus 309 is restricted. Also, on the basis of the lens tube-biological tissue distance d, a warning is issued. For example, in the case in which the lens tube is too close to the biological tissue 311, depending on the distance, the motion speed of the support arm apparatus 309 is restricted while a small-scale warning is also issued, or the motion of the support arm apparatus 309 is stopped while a large-scale warning is also issued.

At this time, in the case in which the scopist 301 is operating the endoscope 307 through the support arm apparatus 309 by a direct operation, the scopist 301 is able to recognize intuitively that the speed of the arm section has decreased, or that the motion of the arm section has stopped. In other words, since the scopist 301 is notified of the positional relationship between the lens tube and the biological tissue 311 more intuitively, the scopist 301 becomes able to respond by changing the operation or the like more rapidly. Thus, the safety of surgery may be improved further.

Note that in the embodiment described above, the motion restriction in the support arm section 120 is executed at the same time as the warning by the output section 160, but the present embodiment is not limited to such an example. In the present embodiment, the support system 1 may also be configured so that at least one of the motion-restricting instruction to the arm control section 130 and the warning instruction to the output section 160 is executed.

Also, the type of motion restriction with respect to the support arm section 120 is not limited to the example described above. In the present embodiment, it is sufficient for the safety control section 170 to issue the motion-restricting instruction so that the scopist may be notified of danger gradually according to the lens tube-biological tissue distance, and the specific content of the motion restriction may be set appropriately. For example, the safety control section 170 may additionally set multiple restricted distances between the first restricted distance and the second restricted distance, and change the allowed speed in the speed restriction control in stages according to the relationship between these multiple restricted distances and the lens tube-biological tissue distance. In other words, the safety control section 170 may issue motion instructions so that the motion speed of the arm section becomes slower as the lens tube approaches a biological tissue. With this arrangement, the scopist becomes able to grasp the positional relationship between the lens tube and the biological tissue even more intuitively, and even further improvement in the safety of surgery may be realized.

Alternatively, in the case in which the driving of the support arm section 120 is controlled by force control, instead of restricting the motion speed, the safety control section 170 may issue a motion-restricting instruction that causes the actuators provided in each joint section of the arm section to operate to apply a sense of resistance to the operation by the scopist. By executing such motion restriction, particularly in the case in which the scopist 301 operates the endoscope 307 by a direct operation with respect to the support arm apparatus 309 as illustrated in FIG. 5, it becomes possible to notify the scopist 301 of the positional relationship between the lens tube and the biological tissue even more intuitively.

(3. Motion-Restricting Information Input Methods)

As described above, in the present embodiment, the motion-restricting information may be input by the user before surgery or during surgery. Herein, several examples of specific methods of inputting motion-restricting information will be described.

Note that in the support system 1, as described above, the motion-restricting information may be input in a non-contact manner by using an NUI. With this arrangement, in the case in which the surgeon or scopist wants to change the motion restriction setting during surgery, it is possible to input the motion-restricting information more smoothly by speech, gaze, or the like, while also continuing one's own work. Consequently, in the following description of methods of inputting motion-restricting information, input methods using an NUI will be described primarily.

Figure 6:
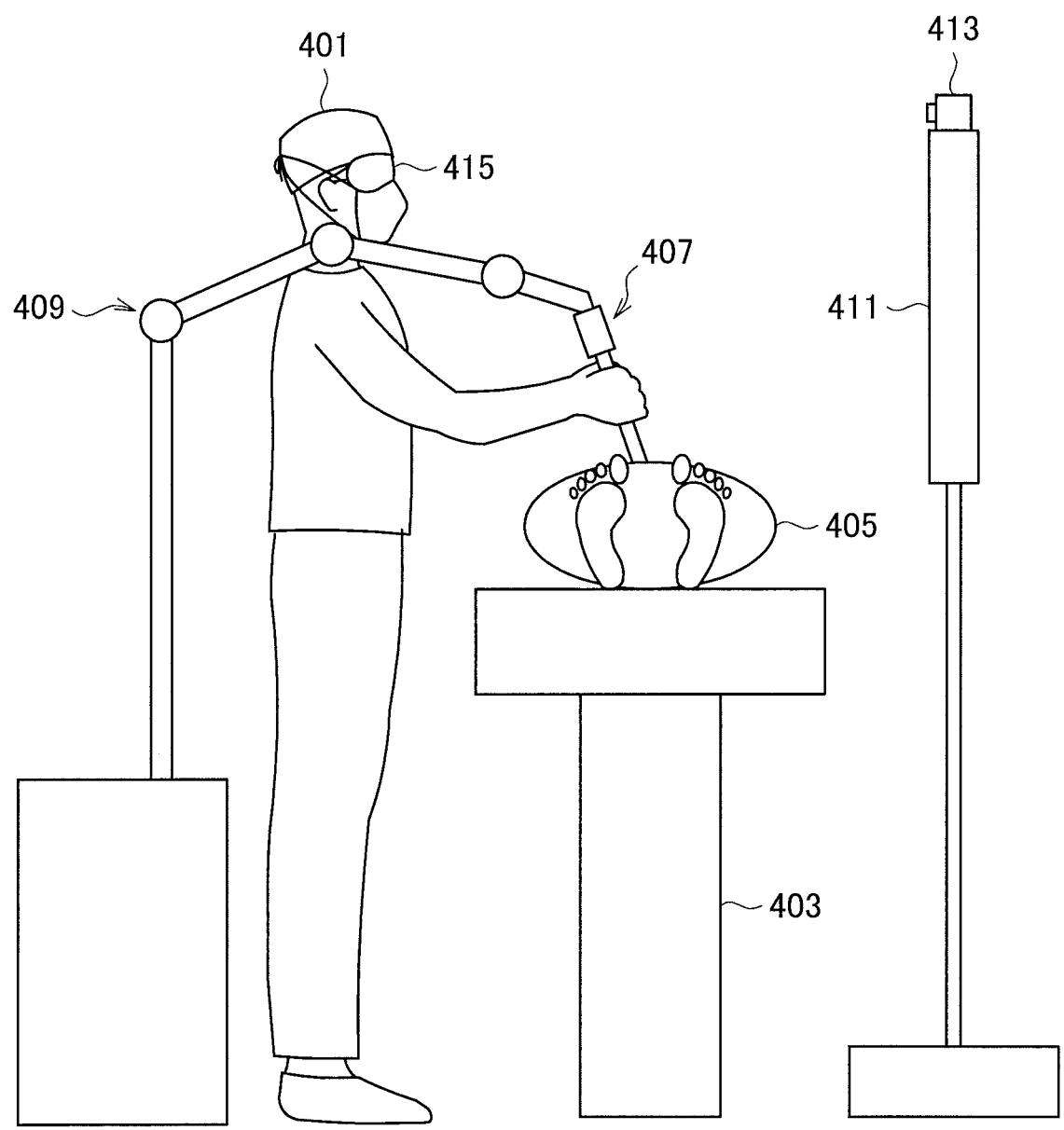
FIG. 6 is a diagram for explaining an NUI in the support system.

FIG. 6 is a diagram for explaining an NUI in the support system 1. FIG. 4 illustrates a state in which a scopist 401 is operating an endoscope 407 with respect to a patient 405 on a patient bed 403. The lens tube of the endoscope 407 supported by a support arm apparatus 409 is inserted into the body cavity of the patient 405, and an image of the operating site captured by the endoscope 407 is displayed on a display apparatus 411 provided inside the operating room. The scopist 401 adjusts the position of the lens tube while referring to the image on the display apparatus 411, so that a desired image is obtained for the operating site. Note that the display apparatus 411 may correspond to the display apparatus 3403 illustrated in FIG. 1. Also, the endoscope 407 and the support arm apparatus 409 may form the endoscope section 110 and the support arm section 120 in FIG. 2.

As described with reference to FIG. 2, in the support system 1, an input apparatus for an NUI may be provided. In the example illustrated in the diagram, a camera apparatus 413 for capturing the state of the scopist 401 (corresponding to the gesture detection section 154 illustrated in FIG. 2) is provided on the upper part of the display apparatus 411. A gesture by the scopist 401 may be detected on the basis of an image captured by the camera apparatus 413.

Also, in the example illustrated in the diagram, the scopist 401 is wearing an eyeglasses-style wearable device 415. The wearable device 415 is provided with a gaze detection sensor (corresponding to the gaze detection section 152 illustrated in FIG. 2) and an acceleration sensor (corresponding to the head tracking detection section 153 illustrated in FIG. 2). The motions of the head of the scopist 401 may be detected on the basis of a detection value of the acceleration sensor. Note that, instead of the wearable device 415, the scopist 401 may also wear an HMD provided with a gaze detection sensor and an acceleration sensor.

Also, the scopist 401 additionally may wear a headset (not illustrated). The speech of the scopist 401 may be detected through a microphone (corresponding to the speech detection section 151 illustrated in FIG. 2) of the headset.

In the support system 1, by appropriately combining these inputs by the gesture, gaze, head tracking, and speech of the scopist 401 with input by other input apparatus (such as a footswitch), smoother input of motion-restricting information becomes possible. Hereinafter, several specific examples of input methods will be described.

For example, information about whether or not to execute a motion restriction may be executed by combining input by speech with input by the footswitch. In this input example, after the scopist 401 switches the mode of the safety control section 170 to the setting mode, by inputting a preset keyword such as "Limit On" by speech, and pressing the footswitch, a motion restriction is applied to the support arm apparatus 409. Also, similarly, by having the scopist 401 input a preset keyword such as "Limit Off" by speech, and then press the footswitch, the motion restriction with respect to the support arm apparatus 409 is released.

Figure 7:
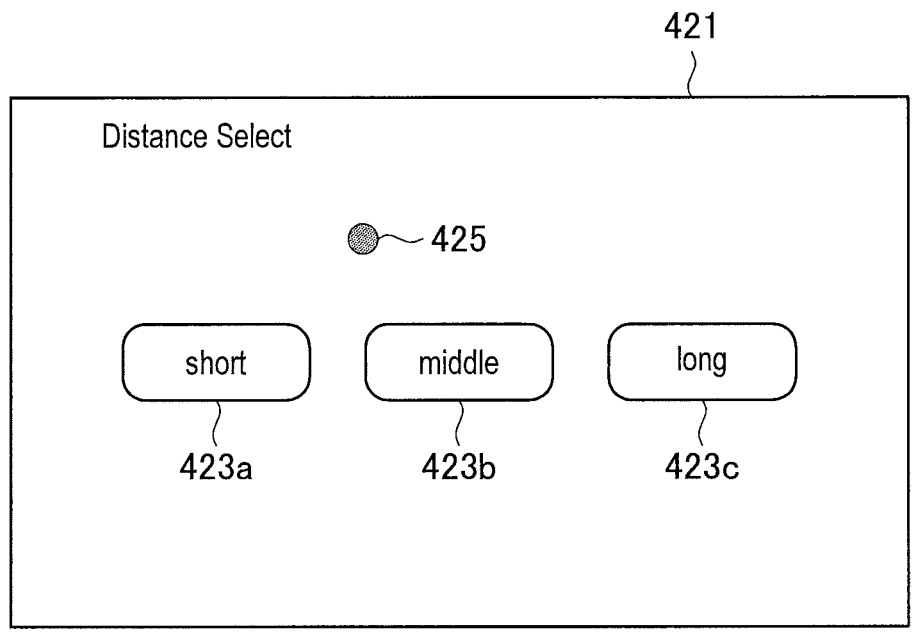
FIG. 7 is a diagram illustrating one display example of a UI when changing the range of a first restricted distance.

Also, for example, information for changing the value of the first restricted distance may be executed by combining input by speech, input by gaze, and input by the footswitch. FIG. 7 is a diagram illustrating one display example of a UI when changing the range of the first restricted distance. For example, if the scopist 401 switches the mode of the safety control section 170 to the setting mode, and then inputs a preset keyword such as "Distance" by speech, a display screen 421 illustrated in FIG. 7 is displayed on the display apparatus 411. In the example illustrated in the diagram, the value of the first restricted distance is settable in three stages, and on the display screen 421, three icons 423*a*, 423*b*, and 423*c* for specifying the value of the first restricted distance are displayed correspondingly. The icon 423*a* is labeled "short" to indicate a comparatively short distance, while the icon 423*b* is labeled "middle" to indicate a moderate distance, and the icon 423*c* is labeled "long" to indicate a comparatively long distance.

In addition, on the display screen 421, a pointer 425 is displayed. It is possible to move the pointer 425 in accordance with the gaze of the scopist 401. The scopist 401 causes the pointer 425 to move by gaze onto one of the icons 423*a*, 423*b*, and 423*c*, in accordance with a desired first restricted distance. By having the scopist 401 press the footswitch while in the state in which one of the icons 423*a*, 423*b*, and 423*c* is selected by the pointer 425, the first restricted distance is changed to the value corresponding to the selected icon.

Figure 8:
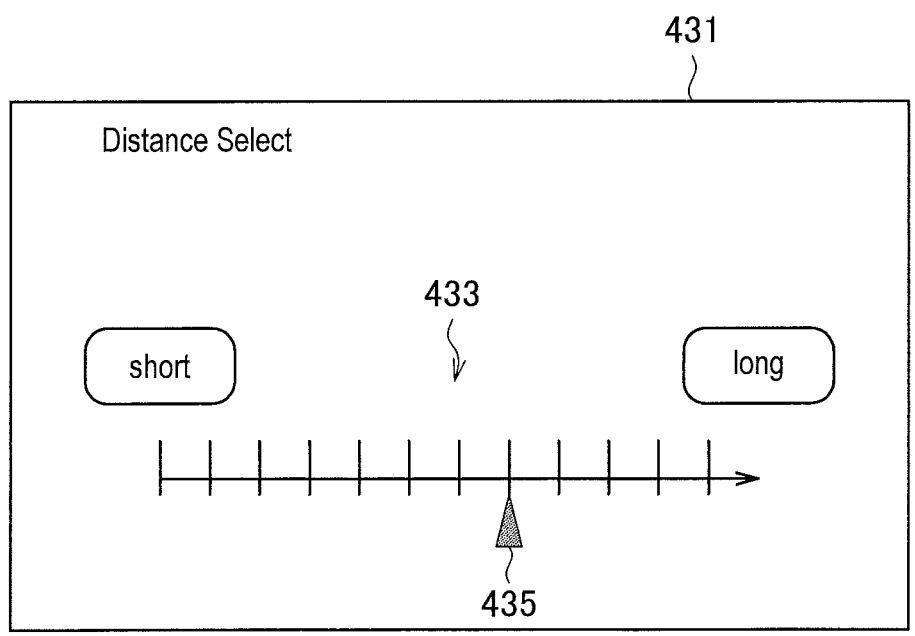
FIG. 8 is a diagram illustrating another display example of a UI when changing the range of the first restricted distance.

Also, as another input method, information for changing the value of the first restricted distance may be executed by combining input by speech, input by head tracking, and input by the footswitch. FIG. 8 is a diagram illustrating another display example of a UI when changing the range of the first restricted distance. In the example illustrated in FIG. 8, there is provided a UI enabling the first restricted distance to be set in a more fine-grained manner than the UI illustrated in FIG. 7.

For example, if the scopist 401 switches the mode of the safety control section 170 to the setting mode, and then inputs a preset keyword such as "Distance" by speech, a display screen 431 illustrated in FIG. 8 is displayed on the display apparatus 411. In the example illustrated in the diagram, the value of the first restricted distance is settable in more stages, and on the display screen 431, a number line 433 with markings for specifying the value of the first restricted distance is displayed correspondingly. The values on the number line 433 correspond to newly set values of the first restricted distance, and indicate that the first restricted distance may be set to a longer distance as one proceeds from one end to the other end.

In addition, on the display screen 431, a pointer 435 is displayed. The pointer 435 is displayed below the number line 433, and can be moved one marking at a time along the number line 433 in accordance with the head tracking of the scopist 401. The scopist 401 causes the pointer 435 to move by head tracking under a desired numerical value on the number line 433, in accordance with a desired first restricted distance. By having the scopist 401 press the footswitch while in the state in which one of the positions on the number line 433 is selected by the pointer 435, the first restricted distance is changed to the value corresponding to the selected position.

The above describes several specific examples of methods of inputting motion-restricting information using an NUI. Note that in the specific examples described above, only information about whether or not to execute a motion restriction and information about the first restricted distance are handled, but obviously it is possible to input other motion-restricting information similarly. For example, the second restricted distance, the advancement region, the peripheral region, the value of the allowed speed when restricting the motion speed, and the like may be set similarly to the methods described with reference to FIG. 7 or FIG. 8. Also, the input methods described above are merely examples, and in the present embodiment, it is possible to input motion-restricting information by an arbitrary method through the input section 150 illustrated in FIG. 2 described earlier. Also, although the description above description the input of motion-restricting information by the scopist 401, the input of motion-restricting information may be executed not only by the scopist 401, but also by another user similarly.

(4. Safety Control Method)

Figure 9:
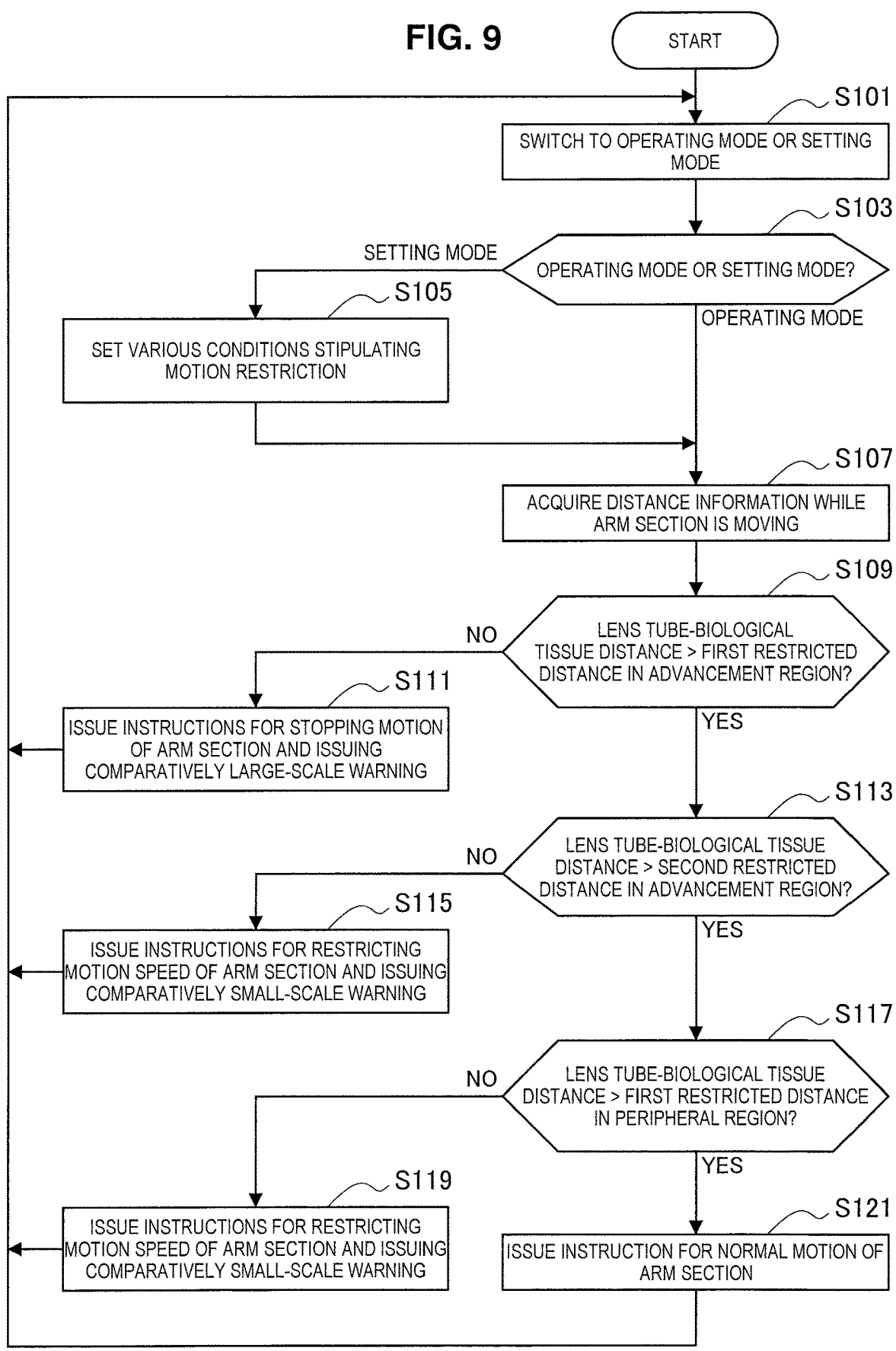
FIG. 9 is a flowchart illustrating an example of a processing procedure of a safety control method according to the present embodiment.

A processing procedure of the safety control method according to the present embodiment will be described with reference to FIG. 9. FIG. 9 is a flowchart illustrating an example of the processing procedure of the safety control method according to the present embodiment. Note that the processes in each step illustrated in FIG. 9 correspond to processes executed by the safety control section 170 illustrated in FIG. 2.

Referring to FIG. 9, in the safety control method according to the present embodiment, first, the mode is switched to the operating mode or the setting mode (step S101). Specifically, in step S101, these modes are switched in accordance with an instruction from the user.

Next, a process of determining whether the mode is the operating mode or the setting mode is executed (step S103). In the case of determining in step S103 that the current mode is the setting mode, on the basis of the motion-restricting information input by the user, various conditions (such as the first restricted distance, the second restricted distance, the advancement region, and the peripheral region, for example) that prescribe the motion restriction (step S105). At this time, the motion-restricting information may be input through an NUI, for example, as described in (3. Motion-restricting information input methods) above.

In the case of determining in step S103 that the current mode is the operating mode, or in the case in which the process of setting the various conditions that prescribe the motion restriction in step S105 has finished, the flow proceeds to step S107. The subsequent processes from step S107 to step S121 are processes executed while the arm section is moving in accordance with an operation by the scopist.

In step S107, distance information about the lens tube-biological tissue distance is acquired while the arm section is moving. Specifically, in step S107, the lens tube-biological tissue distance is computed from a captured image by the image processing distance computation section 140 illustrated in FIG. 2, and information about the lens tube-biological tissue distance is provided to the safety control section 170.

Next, it is determined whether or not the lens tube-biological tissue distance is greater than the first restricted distance inside the advancement region (step S109). The case in which the lens tube-biological tissue distance is less than or equal to the first restricted distance inside the advancement region means that the lens tube is in a state of approaching the biological tissue up to a position that may be dangerous. Consequently, in this case, the flow proceeds to step S111, and an instruction for stopping the motion of the arm section as well as an instruction for executing a comparatively large-scale warning are issued. Specifically, in step S111, the safety control section 170 illustrated in FIG. 2 issues an instruction for stopping the motion of the arm section to the arm control section 130, and issues an instruction for executing the comparatively large-scale warning to the output section 160. By having the arm control section 130 and the output section 160 operate in accordance with these instructions, the motion of the arm section is stopped, and the comparatively large-scale warning is executed.

On the other hand, in the case of determining in step S109 that the lens tube-biological tissue distance is greater than the first restricted distance inside the advancement region, the flow proceeds to step S113. In step S113, it is determined whether or not the lens tube-biological tissue distance is greater than the second restricted distance inside the advancement region. The case in which the lens tube-biological tissue distance is less than or equal to the second restricted distance inside the advancement region means that, although the lens tube has not yet approached up to the first restricted distance, the lens tube is in a state of approaching the biological tissue, and thus there is a risk that further movement of the lens tube may be dangerous. Consequently, in this case, the flow proceeds to step S115, and an instruction for restricting the motion of the arm section as well as an instruction for executing a comparatively small-scale warning are issued. Specifically, in step S115, the safety control section 170 illustrated in FIG. 2 issues an instruction for restricting the motion speed of the arm section to the arm control section 130, and issues an instruction for executing the comparatively small-scale warning to the output section 160. By having the arm control section 130 and the output section 160 operate in accordance with these instructions, the motion speed of the arm section is restricted, and the comparatively small-scale warning is executed.

In the case of determining in step S113 that the lens tube-biological tissue distance is greater than the second restricted distance inside the advancement region, the flow proceeds to step S117. In step S117, it is determined whether or not the lens tube-biological tissue distance is greater than the first restricted distance inside the peripheral region. The case in which the lens tube-biological tissue distance is less than or equal to the second restricted distance inside the peripheral region means that, although there is a low possibility of danger occurring if the lens tube continues to advance in the same direction, biological tissue exists relatively close to the lens tube. Consequently, in this case, the flow proceeds to step S119, and an instruction for restricting the motion of the arm section as well as an instruction for executing a comparatively small-scale warning are issued. Specifically, in step S119, similarly to step S115, the safety control section 170 illustrated in FIG. 2 issues an instruction for restricting the motion speed of the arm section to the arm control section 130, and issues an instruction for executing the comparatively small-scale warning to the output section 160. By having the arm control section 130 and the output section 160 operate in accordance with these instructions, the motion speed of the arm section is restricted, and the comparatively small-scale warning is executed.

In the case of determining in step S117 that the lens tube-biological tissue distance is greater than the first restricted distance inside the peripheral region, the flow proceeds to step S121. In step S121, an instruction for causing normal motion in the arm section is issued. Specifically, in step S121, the safety control section 170 illustrated in FIG. 2 issues an instruction for causing normal motion in the arm section to the arm control section 130. By having the arm control section 130 operate in accordance with the instruction, normal motion of the arm section is executed.

When the process in step S111, step S115, step S117, or step S121 finishes, the flow returns to step S101. Subsequently, the series of processes described above is executed repeatedly during surgery.

The above describes a processing procedure of the safety control method according to the present embodiment. Note that in the process in step S111, after the instruction for stopping the motion of the arm section and the instruction for executing the comparatively large-scale warning are issued, a motion-restricting instruction for causing the arm section to operate so that the lens tube is movable while the motion speed is restricted only in the direction that increases the lens tube-biological tissue distance additionally may be issued. With this arrangement, even in the case in which the instruction for stopping the motion of the arm section is issued, it is possible to cause the lens tube to move in a state in which safety is ensured, without having to return to step S101 to step S105 are input an instruction for releasing the motion restriction in the setting mode, thereby making it possible to proceed with surgery more smoothly.

(5. Modifications)

Several modifications of the embodiment described above will be described. Note that the configuration according to the embodiment described above and the configuration related to each modification described below may also be combined with each other where possible.

(5-1. Distance Measurement Method)

In the embodiment described above, the endoscope is configured as a stereo camera, and the lens tube-biological tissue distance is detected on the basis of the captured image therefrom. However, the present embodiment is not limited to such an example, and the lens tube-biological tissue distance may also be detected by another method. Herein, as a modification of the present embodiment, a configuration of the support system in the case in which another distance measurement method is applied, and a process executed in the support system, will be described. Note that the support system according to the present modification still may be applied to the endoscopic surgery system 3000 illustrated in FIG. 1, similarly to the embodiment described above.

(5-1-1. Case in which Distance Measurement Sensor is Provided on Front End of Lens Tube)

Figure 10:
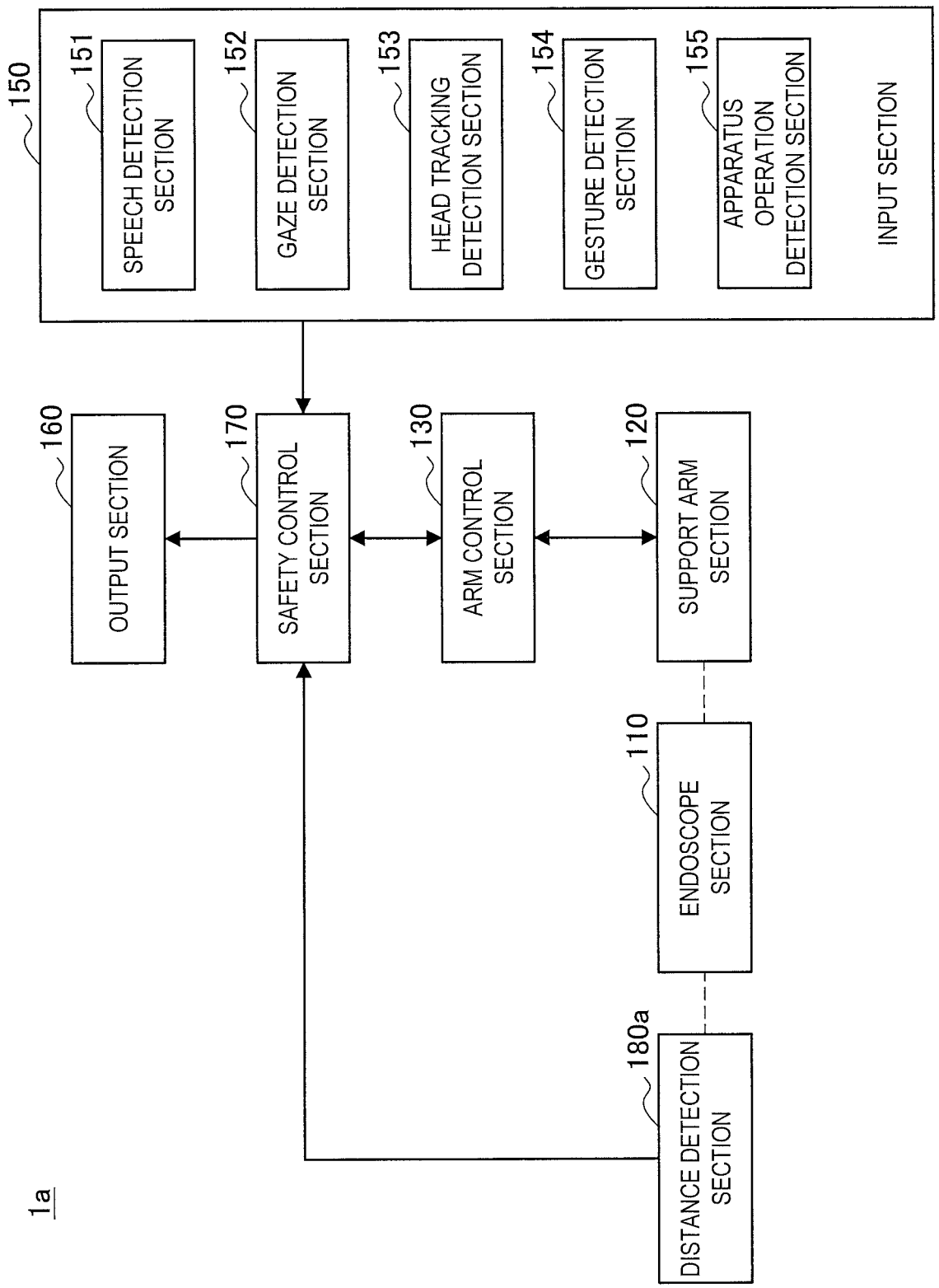
FIG. 10 is a block diagram illustrating an example of a functional configuration of a support system according to a modification in which a distance measurement sensor is provided on the front end of an endoscope.

For example, a distance measurement sensor may be provided on the front end of the lens tube of the endoscope. FIG. 10 is a block diagram illustrating an example of a functional configuration of a support system according to such a modification in which a distance measurement sensor is provided on the front end of an endoscope.

Referring to FIG. 10, the support system 1*a* according to the present modification is provided with the endoscope section 110, the support arm section 120, the arm control section 130, the input section 150, the output section 160, the safety control section 170, and a distance detection section 180*a* as functions thereof. Note that the support system 1*a* according to the present modification has a configuration approximately similar to the support system 1 illustrated in FIG. 2, except that the method of measuring the lens tube-biological tissue distance is different, and correspondingly the processes in the safety control section 170 are different. Consequently, in the following description of the support system 1*a*, the differences from the support system 1 will be described primarily, whereas detailed description will be omitted for items that overlap.

As illustrated in FIG. 10, the support system 1*a* does not include the function of the image processing distance computation section 140 provided in the support system 1. Instead, the support system 1*a* is provided with the function of the distance detection section 180*a*.

The distance detection section 180*a* detects the distance between the front end of the lens tube of the endoscope section 110, and a biological tissue existing in the advancement direction of the lens tube. The function of the distance detection section 180*a* may be realized by a distance measurement sensor provided on the front end of the lens tube of the endoscope section 110. The type of the distance measurement sensor is not limited, and any of various known types of sensors may be used, such as an infrared sensor or an ultrasonic sensor, for example. The distance detection section 180*a* provides information about the detected lens tube-biological tissue distance to the safety control section 170. Note that in FIG. 10, to indicate that the distance detection section 180*a* may be provided on the front end of the lens tube of the endoscope section 110, the two sections are joined by a dashed line.

Herein, generally, with distance measurement by a distance measurement sensor, planar distance measurement cannot be executed like distance measurement based on a captured image from a stereo camera, and the distance to a predetermined point serving as a target can be detected. Hereinafter, for the sake of convenience, such distance measurement that detects the distance to a predetermined point serving as a target is also called 1-point distance measurement.

Figure 11:
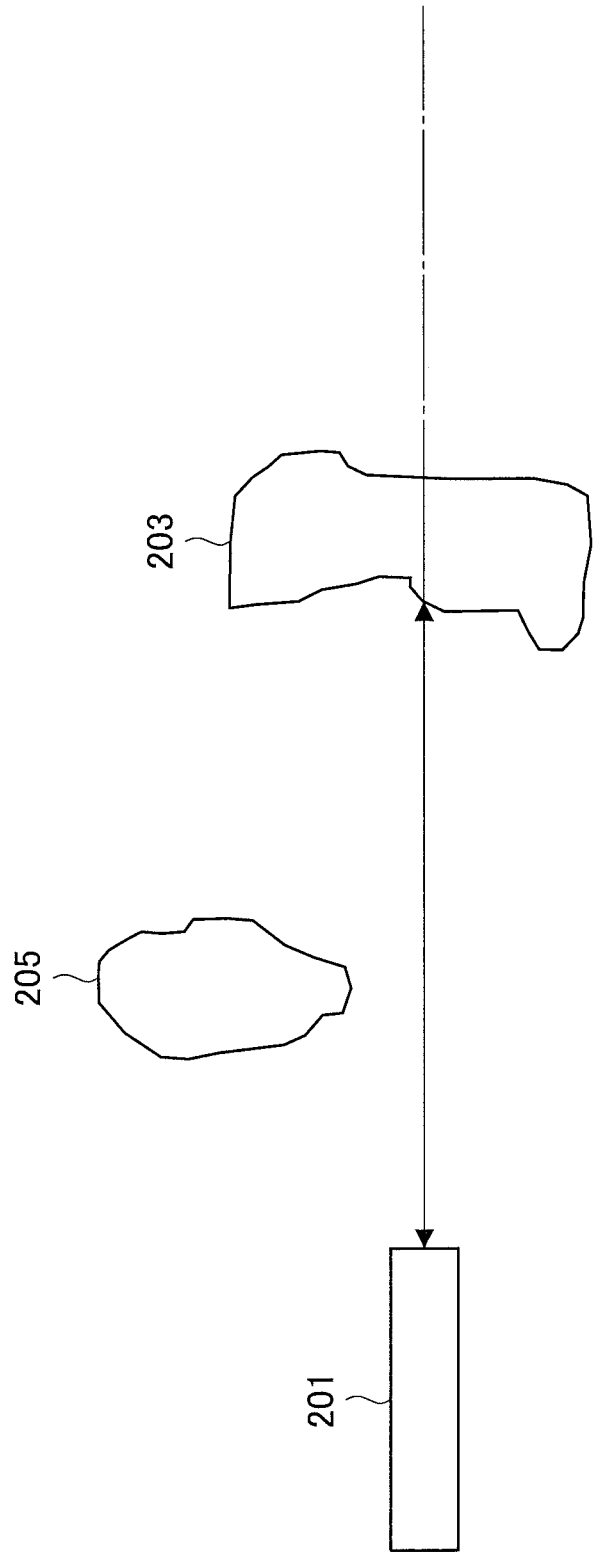
FIG. 11 is a diagram schematically illustrating a state of 1-point distance measurement.

FIG. 11 is a diagram schematically illustrating a state of 1-point distance measurement. Similarly to FIG. 3, FIG. 11 illustrates, inside the body cavity, the positional relationships of the lens tube 201, the biological tissue 203 positioned in front in the advancement direction of the lens tube 201, and the other biological tissue 205 which is positioned in the advancement direction of the lens tube 201, but is positioned in a location away from the front.

As described with reference to FIG. 3, in the above embodiment, since it is possible to execute planar distance measurement, a two-dimensional distribution of the lens tube-biological tissue distance can be obtained. On the other hand, as illustrated in FIG. 11, in the present modification, only the distance between the front end of the lens tube 201 and a single point in the extension direction of the lens tube 201 may be detected. In other words, in the present modification, although the distance between the lens tube 201 and the biological tissue 203 can be detected, the distance between the lens tube 201 and the other biological tissue 205 cannot be detected. For this reason, the safety control section 170 is also provided with information about the distance between the front end of the lens tube 201 and a predetermined point on the surface of the biological tissue 205 detected by 1-point distance measurement as the information about the lens tube-biological tissue distance. In this way, in the present modification, since only the lens tube-biological tissue distance at a single point may be detected, it is difficult to set an advancement region and a peripheral region, and determine the lens tube-biological tissue distance for each of these regions like in the embodiment described above.

Figure 12:
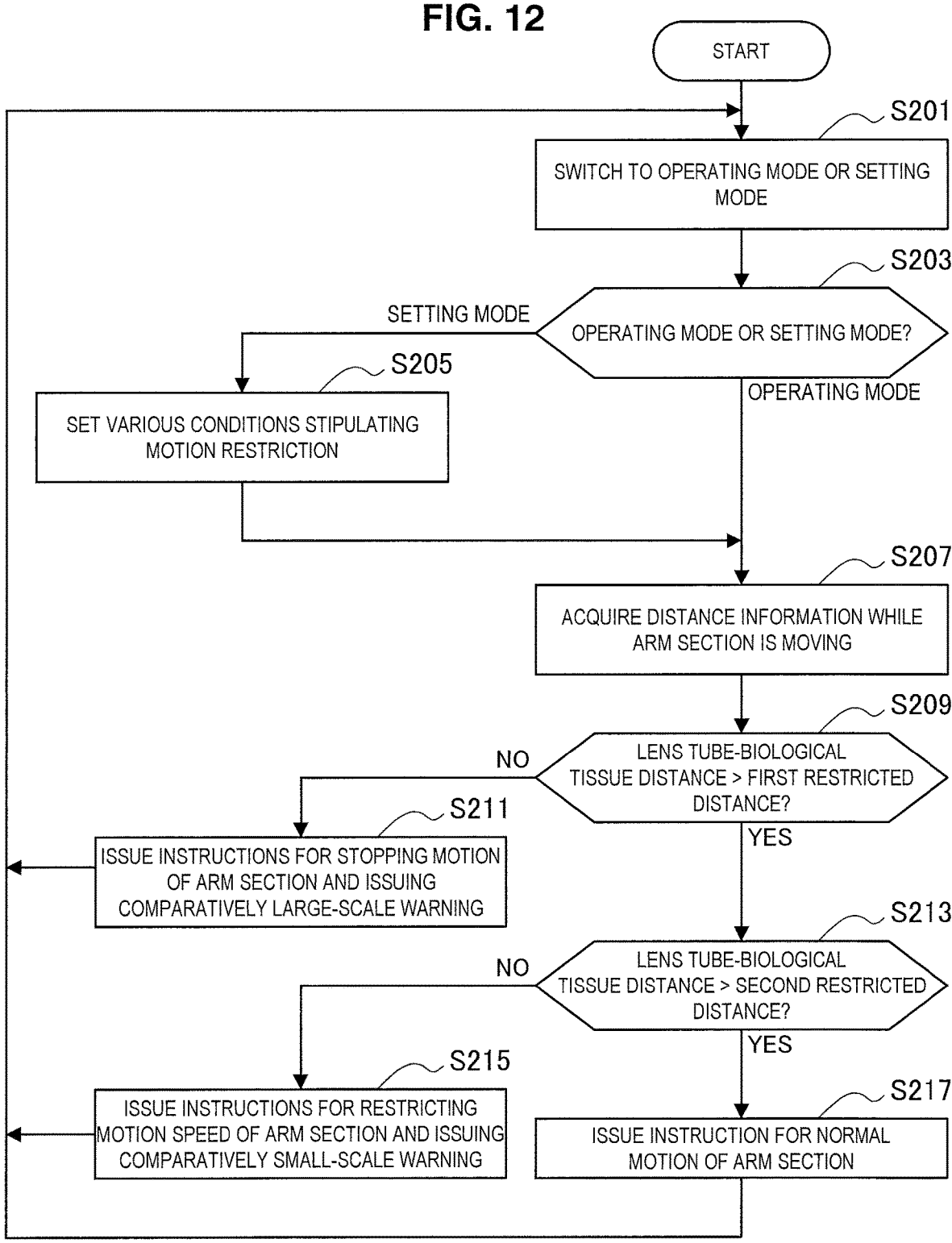
FIG. 12 is a flowchart illustrating an example of a processing procedure of a safety control method according to a modification in which a distance measurement sensor is provided on the front end of an endoscope.

Consequently, in the present modification, the processes in the safety control section 170 are changed from the embodiment described earlier. FIG. 12 is a flowchart illustrating an example of the processing procedure of the safety control method according to the present modification. Note that the processes in each step illustrated in FIG. 12 correspond to processes executed by the safety control section 170 illustrated in FIG. 11.

Referring to FIG. 12, in the safety control method according to the present modification, the processes from step S201 to step S207 are substantially similar to the processes from step S101 to step S107 in the safety control method according to the embodiment described earlier and illustrated in FIG. 9. Namely, first, the mode is switched to the operating mode or the setting mode (step S201), and then a mode determination process is executed (step S203). Subsequently, in the case of the setting mode, various conditions that prescribe a motion restriction are set (step S205). However, in step S205, unlike step S105, the advancement region and the peripheral region are not set. Next, distance information about the lens tube-biological tissue distance is acquired while the arm section is moving (step S207). However, in step S207, information about the lens tube-biological tissue distance detected by 1-point distance measurement by the distance detection section 180*a* illustrated in FIG. 10 is provided to the safety control section 170.

In the present modification, the following processes greatly differ from the embodiment described earlier. Specifically, in the present modification, next, it is determined whether or not the lens tube-biological tissue distance is greater than the first restricted distance (step S209). The case in which the lens tube-biological tissue distance is less than or equal to the first restricted distance means that the lens tube is in a state of approaching the biological tissue up to a position that may be dangerous. Consequently, in this case, the flow proceeds to step S211, and an instruction for stopping the motion of the arm section as well as an instruction for executing a comparatively large-scale warning are issued. Specifically, in step S211, the safety control section 170 illustrated in FIG. 10 issues an instruction for stopping the motion of the arm section to the arm control section 130, and issues an instruction for executing the comparatively large-scale warning to the output section 160. By having the arm control section 130 and the output section 160 operate in accordance with these instructions, the motion of the arm section is stopped, and the comparatively large-scale warning is executed. Note that, similarly to the embodiment described earlier, in the process in step S211, after the instruction for stopping the motion of the arm section and the instruction for executing the comparatively large-scale warning are issued, a motion-restricting instruction for causing the arm section to operate so that the lens tube is movable while the motion speed is restricted only in the direction that increases the lens tube-biological tissue distance additionally may be issued.

On the other hand, in the case of determining in step S109 that the lens tube-biological tissue distance is greater than the first restricted distance, the flow proceeds to step S213. In step S213, it is determined whether or not the lens tube-biological tissue distance is greater than the second restricted distance. The case in which the lens tube-biological tissue distance is less than or equal to the second restricted distance means that, although the lens tube has not yet approached up to the first restricted distance, the lens tube is in a state of approaching the biological tissue, and thus there is a risk that further movement of the lens tube may be dangerous. Consequently, in this case, the flow proceeds to step S215, and an instruction for restricting the motion of the arm section as well as an instruction for executing a comparatively small-scale warning are issued. Specifically, in step S215, the safety control section 170 illustrated in FIG. 10 issues an instruction for restricting the motion speed of the arm section to the arm control section 130, and issues an instruction for executing the comparatively small-scale warning to the output section 160. By having the arm control section 130 and the output section 160 operate in accordance with these instructions, the motion speed of the arm section is restricted, and the comparatively small-scale warning is executed.

In the case of determining in step S213 that the lens tube-biological tissue distance is greater than the second restricted distance, the flow proceeds to step S217. In step S217, an instruction for causing normal motion in the arm section is issued. Specifically, in step S217, the safety control section 170 illustrated in FIG. 10 issues an instruction for causing normal motion in the arm section to the arm control section 130. By having the arm control section 130 operate in accordance with the instruction, normal motion of the arm section is executed.

When the process in step S211, step S215, or step S217 finishes, the flow returns to step S201. Subsequently, the series of processes described above is executed repeatedly during surgery.

As described above, according to the present modification, a process of determining whether or not to restrict the motion of the arm section is executed, without considering the advancement region and the peripheral region. Even with such a safety control method that does not consider the advancement region and the peripheral region, since the motion of the arm section is restricted on the basis of the lens tube-biological tissue distance targeting a predetermined point in the advancement direction of the lens tube, it is possible to effectively prevent contact between the lens tube and a biological tissue in the advancement direction of the lens tube. In this way, even in the case in which the endoscope is not configured as a stereo camera, and a distance measurement sensor is used to detect the lens tube-biological tissue distance, for example, it is possible to obtain an effect of further increasing the safety of surgery, similarly to the embodiment described earlier.

(5-1-2. Case in which Distance Detection Section is Provided Externally)

Figure 13:
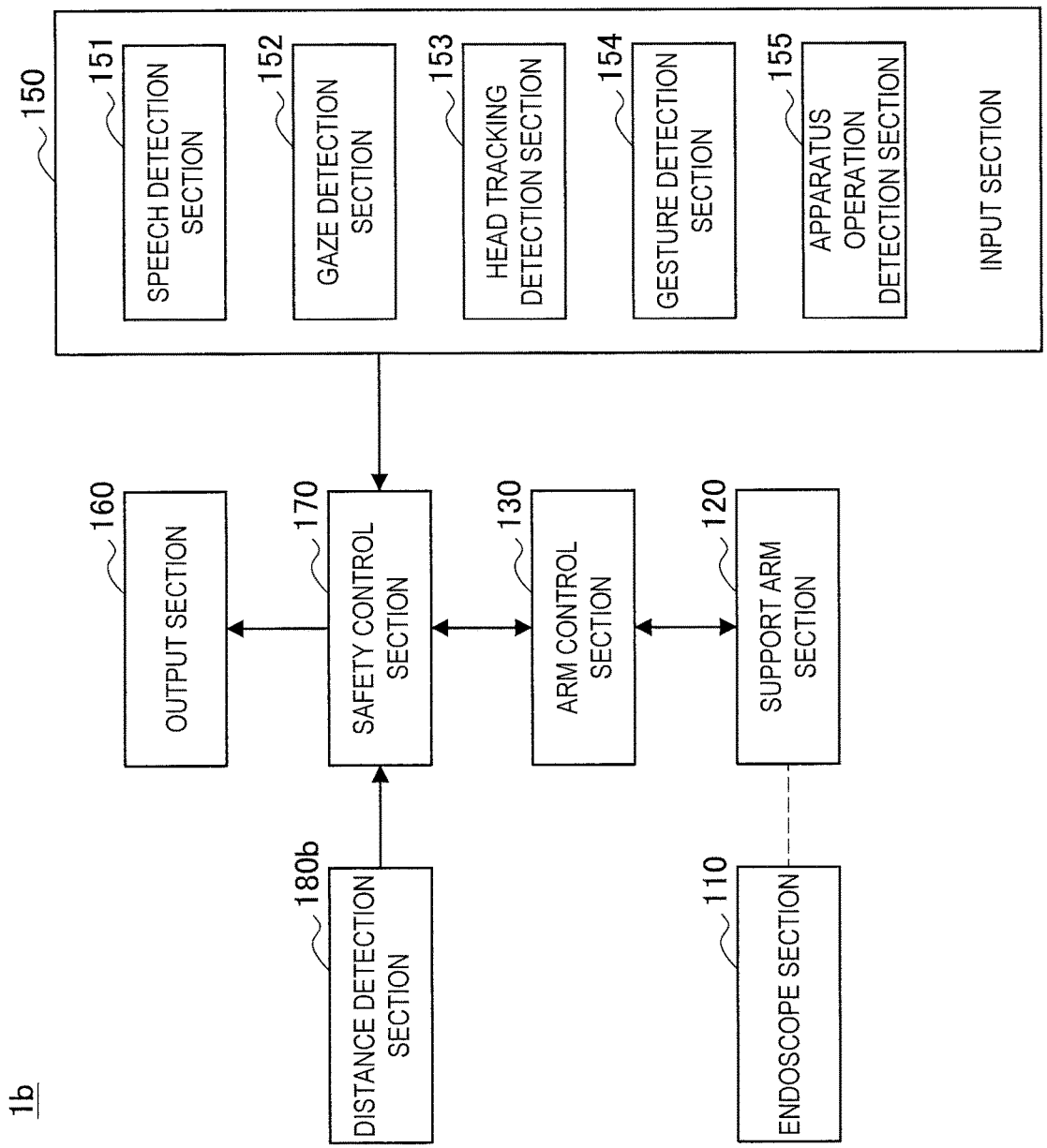
FIG. 13 is a block diagram illustrating an example of a functional configuration of a support system according to a modification in which a distance detection section that observes the lens tube of an endoscope from the outside is provided.

As yet another distance measurement method, a method is conceivable in which a distance detection section is provided at a position where the lens tube of the endoscope may be observed from the outside, and the lens tube-biological tissue distance is detected by the distance detection section. FIG. 13 is a block diagram illustrating an example of a functional configuration of a support system according to a modification in which such a distance detection section that observes the lens tube of an endoscope from the outside is provided.

Referring to FIG. 13, the support system 1b according to the present modification is provided with the endoscope section 110, the support arm section 120, the arm control section 130, the input section 150, the output section 160, the safety control section 170, and a distance detection section 180b as functions thereof. Note that the support system 1b according to the present modification has a configuration approximately similar to the support system 1 illustrated in FIG. 2, except that the method of measuring the lens tube-biological tissue distance is different, and correspondingly the processes in the safety control section 170 are different. Consequently, in the following description of the support system 1b, the differences from the support system 1 will be described primarily, whereas detailed description will be omitted for items that overlap.

As illustrated in FIG. 13, the support system 1b does not include the function of the image processing distance computation section 140 provided in the support system 1. Instead, the support system 1b is provided with the function of the distance detection section 180b.

The distance detection section 180b detects the distance between the front end of the lens tube of the endoscope section 110, and a biological tissue existing in the advancement direction of the lens tube. The function of the distance detection section 180b may be realized by a distance measurement sensor provided at a position where the lens tube of the endoscope section 110 and the biological tissue positioned in the advancement direction of the lens tube may be observed, for example. The distance measurement sensor is inserted into the body cavity of the patient separately from the lens tube of the endoscope section 110, other surgical instruments, and the like, for example. Any of various known types of sensors (such as an ultrasonic sensor, for example) capable of measuring the distance between two points in space may be applied as the distance measurement sensor. Alternatively, the function of the distance detection section 180b may be realized by another endoscope different from the endoscope section 110. If the other endoscope is configured as a stereo camera, by inserting the lens tube of the other endoscope up to a position where the lens tube of the endoscope section 110 and the biological tissue positioned in the advancement direction of the lens tube may be observed, and acquiring a captured image with an angle of view that includes the lens tube of the endoscope section 110 and the biological tissue, the distance between the lens tube of the endoscope section 110 and the biological tissue can be detected from the captured image. The distance detection section 180b provides information about the detected lens tube-biological tissue distance to the safety control section 170.

Herein, in the present modification, the distance detection section 180b may be configured to be capable of executing planar distance measurement, or may be configured to be capable of executing 1-point distance measurement. In the case in which the distance detection section 180*b* is configured to be capable of executing planar distance measurement, the safety control section 170 is able to execute the safety control method in accordance with the processing procedure illustrated in FIG. 9. Also, in the case in which the distance detection section 180*b* is configured to be capable of executing 1-point distance measurement, the safety control section 170 is able to execute the safety control method in accordance with the processing procedure illustrated in FIG. 12. In this way, in the present modification, the safety control method illustrated in FIG. 9 or FIG. 12 may be executed as appropriate, according to the configuration of the distance detection section 180*b*.

As described above, even in the case of detecting the lens tube-biological tissue distance by a distance detection section 180 provided on the outside like the present modification, it is possible to execute a safety control method similar to the embodiment described above or the modification described above. Consequently, in the present modification, it is possible to obtain an effect of further raising the safety of surgery, similarly to the embodiment described above.

Note that in the case in which the endoscope is an oblique-viewing scope or a side-viewing scope, in the distance measurement based on a captured image from a stereo camera, the distance between the front end of the lens tube of the endoscope and a biological tissue existing in the advancement direction of the lens tube cannot be measured. In contrast, according to the modification described above, even if the endoscope is an oblique-viewing scope or a side-viewing scope, it is possible to measure the distance between the front end of the lens tube of the endoscope and a biological tissue existing in the advancement direction of the lens tube. In this way, the modification according to the other distance measurement method described above may be applied to the case in which the endoscope is an oblique-viewing scope or a side-viewing scope.

(5-2. Retracting Motion)

In the embodiment described above, the stopping of motion and the restriction of the motion speed are executed as motion restrictions with respect to the arm section. However, the types of motion restriction are not limited to such an example, an in the present embodiment, other motion restrictions may be executed.

For example, in the case in which the lens tube-biological tissue distance is comparatively small (for example, in the case in which the lens tube approaches the biological tissue up to the first restricted distance or less), the motion of the arm section may be controlled so that the lens tube moves away from the biological tissue (retracting motion).

For example, in the embodiment described above, when restricting the motion of the arm section, the retracting motion may be executed instead of stopping the motion. With this arrangement, in the case in which the lens tube has approached the biological tissue closer than the first restricted distance, it is possible to not only stop the motion of the lens tube, but also to cause the lens tube to move away from the biological tissue. Consequently, it becomes possible to further increase the safety of surgery.

Note that at this time, in the retracting motion, it is preferable for the lens tube to automatically move backward a fixed distance along the path on which the lens tube has advanced. The path on which the lens tube has advanced is a path the lens tube has already passed through, and thus may be considered a path on which safety is ensured.

Consequently, even if the lens tube executes the retracting motion automatically, the motion does not pose a danger to the patient.

A support system according to a modification in which such a retracting motion is executed as the motion restriction is realizable by a functional configuration similar to the support system 1 according to the embodiment described earlier and illustrated in FIG. 2. Consequently, a description of the functional configuration of the support system according to the present modification will be omitted. However, in the support system according to the present modification, the processes in the safety control section 170 are different from the embodiment described earlier.

Figure 14:
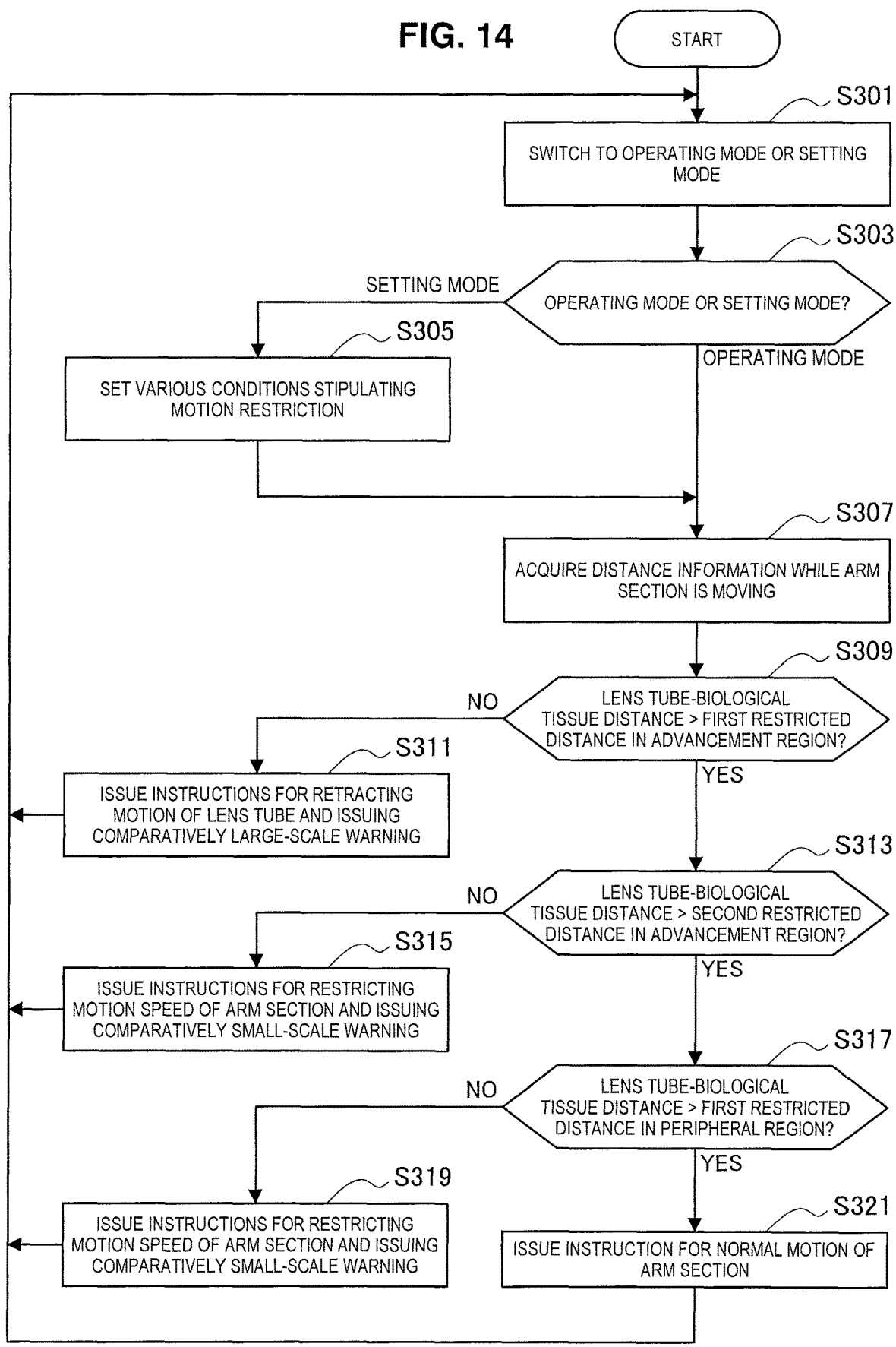
FIG. 14 is a flowchart illustrating an example of a processing procedure of a safety control method according to a modification in which a retracting motion is executed as the motion restriction.

FIG. 14 will be referenced to describe processes in the safety control section according to the present modification. FIG. 14 is a flowchart illustrating an example of a processing procedure of the safety control method according to the modification in which the retracting motion is executed as the motion restriction.

Referring to FIG. 14, in the safety control method according to the present modification, the processes from step S301 to step S309 and from step S313 to step S321 are substantially similar to the processes from step S101 to step S109 and from step S113 to step S121 in the safety control method according to the embodiment described earlier and illustrated in FIG. 9. Consequently, a detailed description of these processes will be omitted.

In the present modification, in the case of determining in step S309 that the lens tube-biological tissue distance is less than or equal to the first restricted distance inside the advancement region, an instruction for retracting the lens tube and an instruction for executing a comparatively large-scale warning are issued (step S311). Specifically, in step S311, the safety control section 170 illustrated in FIG. 2 issues an instruction for causing the arm section to execute the retracting motion to the arm control section 130, and issues an instruction for executing the comparatively large-scale warning to the output section 160. By having the arm control section 130 and the output section 160 operate in accordance with these instructions, the retracting motion of the lens tube and the comparatively large-scale warning are executed.

Herein, the processing procedure illustrated in FIG. 14 corresponds to the case in which the support system is configured to be capable of executing planar distance measurement, similarly to the embodiment described earlier. However, the present modification is not limited to such an example, and is also applicable to a support system configured to be capable of executing 1-point distance measurement, as described in (5-1-1. Case in which distance measurement sensor is provided on front end of lens tube) above. In other words, the support system according to the present modification may be realized by a functional configuration similar to the support system 1*a* illustrated in FIG. 10.

Figure 15:
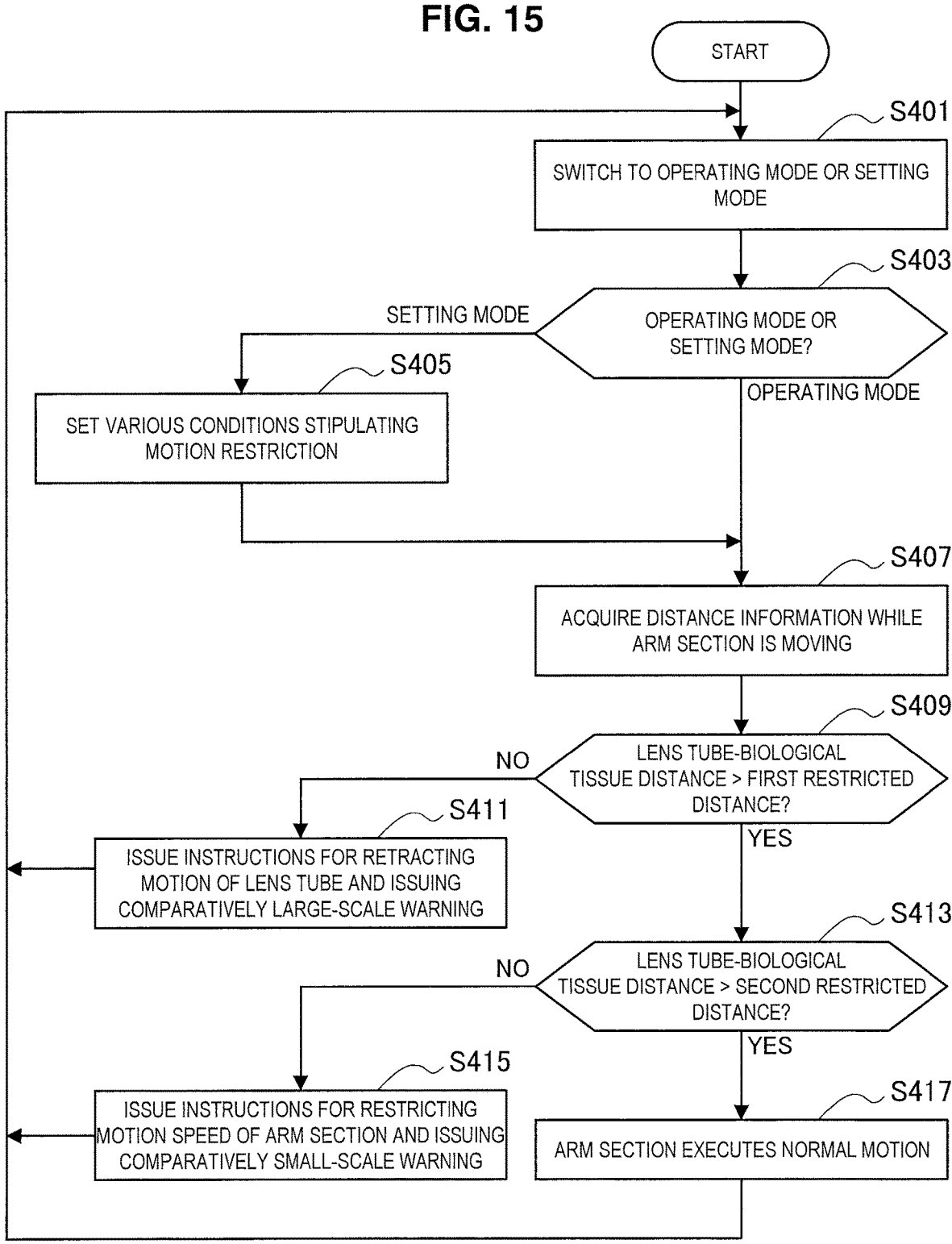
FIG. 15 is a flowchart illustrating another example of a processing procedure of a safety control method according to a modification in which a retracting motion is executed as the motion restriction.

Processes in the safety control section 170 in this case will be described with reference to FIG. 15. FIG. 15 is a flowchart illustrating another example of a processing procedure of the safety control method according to the modification in which the retracting motion is executed as the motion restriction.

Referring to FIG. 15, in the safety control method according to the present modification, the processes from step S401 to step S409 and from step S413 to step S417 are substantially similar to the processes from step S201 to step S209 and from step S213 to step S217 in the safety control method according to the modification illustrated in FIG. 12 in which a distance measurement sensor is provided on the front end of the lens tube. Consequently, a detailed description of these processes will be omitted.

In the present modification, in the case of determining in step S409 that the lens tube-biological tissue distance is less than or equal to the first restricted distance, an instruction for retracting the lens tube and an instruction for executing a comparatively large-scale warning are issued (step S411). Specifically, in step S411, the safety control section 170 illustrated in FIG. 10 issues an instruction for causing the arm section to execute the retracting motion to the arm control section 130, and issues an instruction for executing the comparatively large-scale warning to the output section 160. By having the arm control section 130 and the output section 160 operate in accordance with these instructions, the retracting motion of the lens tube and the comparatively large-scale warning are executed.

As described above, according to the present modification, by executing the retracting motion of the lens tube in the case of a comparatively small lens tube-biological tissue distance, it becomes possible to ensure the safety of surgery further. Also, in this case, the present modification is applicable regardless of the distance measurement method.

(5-3. Operation of Other Configurations Through NUI)

In the embodiment described earlier, the motion-restricting information can be input through an NUI. However, the present embodiment is not limited to such an example, and operation input may also be possible with respect to other configurations of the endoscopic surgery system 3000 illustrated in FIG. 1 through an NUI.

FIG. 16 is a block diagram illustrating an example of a functional configuration of a support system configured to allow operation input with respect to other configurations of the endoscopic surgery system 3000 through an NUI.

Referring to FIG. 16, the support system 1c according to the present modification is provided with the endoscope section 110, the support arm section 120, the arm control section 130, the image processing distance computation section 140, the input section 150, the output section 160, the safety control section 170, an imaging control section 181, and a display control section 182 as functions thereof. Note that the support system 1c according to the present modification has a configuration approximately similar to the support system 1 illustrated in FIG. 2, except that the functions of the arm control section 130 and the image processing distance computation section 140 are partially changed, and the functions of the imaging control section 181 and the display control section 182 are added. Consequently, in the following description of the support system 1c according to the present modification, the differences from the support system 1c will be described primarily, whereas detailed description will be omitted for items that overlap.

In the support system 1c, the imaging conditions (such as the type of irradiating light, the magnification, and/or the focal length) in the endoscope section 110 are configured to be changeable by operation input from the input section 150. Specifically, the support system 1c is provided with the imaging control section 181 that controls the imaging conditions in the endoscope section 110 as a function thereof, and information about operation input of the user with respect to the endoscope section 110 is provided from the input section 150 to the imaging control section 181. The imaging control section 181, following the user instructions, appropriately controls the imaging conditions of the endoscope section 110. Note that the function of the imaging control section 181 may be realized by the CCU 3401 illustrated in FIG. 1.

Also, in the support system 1c, the arm section of the support arm section 120 is configured to be operable by operation input from the input section 150. In other words, the arm section may be operated by operation input other than a direct operation. Specifically, in the support system 1c, information about the operation input of the user with respect to the arm section is provided from the input section 150 to the arm control section 130. The arm control section 130, following the user instructions, appropriately controls the motion of the arm section.

Also, in the support system 1c, the display on the display apparatus (corresponding to the display apparatus 3403 illustrated in FIG. 1) that forms the output section 160 is configured to be operable by operation input from the input section 150. Specifically, in the support system 1c, the image processing distance computation section 140 performs the process of computing the lens tube-biological tissue distance, as well as various types of image processing (such as a development process, for example) with respect to the image signal acquired by the endoscope section 110 to display an image based the image signal on the display apparatus. Subsequently, the image processing distance computation section 140 provides the image signal on which the image processing has been performed to the display control section 182. The display control section 182 includes a function of driving and controlling the display of the display apparatus forming the output section 160, and causes the display apparatus to display a captured image on the basis of the image signal. In the present modification, information about the operation input of the user with respect to the display apparatus is provided from the input section 150 to the display control section 182. The display control section 182, following the user instructions, appropriately controls the display on the display apparatus. For example, according to an operation by the user, the magnification, brightness, and the like of the displayed image may be changed. Note that the function of the display control section 182 may be realized by the CCU 3401 illustrated in FIG. 1.

Note that the functions of the imaging control section 181 and the display control section 182 described above are functions originally provided in the endoscopic surgery system 3000 illustrated in FIG. 1. In other words, in FIG. 16, these functions are explicitly illustrated for the sake of explanation, but the control of the imaging conditions of the endoscope section 110 by the imaging control section 181 and the control of the display on the display apparatus by the display control section 182 may also be executed similarly in the support systems according to the embodiment and the modifications described above. In other words, the present modification enables control of the functions originally provided in the endoscopic surgery system 3000 by an operation input method (for example, operation input through an NUI) which is newly introduced by applying the support system 1c.

As described above, according to the present modification, by operation input through an NUI, it is possible to appropriately operate the imaging conditions of the endoscope section 110, the motion of the arm section of the support arm section 120, and the display on the display apparatus forming the output section 160. By using the NUI, it becomes possible to execute operation input in a non-contact manner, and thus even a user belonging to a clean area is able to execute operation input without touching an input apparatus belonging to an unclean area, for example. Also, since operation input can be executed more intuitively with a simpler operation, various types of operation input can be executed without stopping one's hand in the work. Consequently, by having each configuration in the endoscopic surgery system 3000 be operable through the NUI like the present modification, it becomes possible to increase user convenience remarkably.

(5-4. Application to Support Arm Apparatus of Master-Slave Method)

In the embodiment described above, the support arm apparatus that supports the endoscope is configured to be operable by a direct operation by the scopist. However, the present embodiment is not limited to such an example. As described in (1. Configuration of endoscopic surgery system) above, the support arm apparatus to which the support system according to the present embodiment may be applied may also be configured to be operable by the master-slave method.

Even in the case in which the support arm apparatus is configured to be operable by the master-slave method, by the configuration of the support system 1 illustrated in FIG. 2, for example, it is possible to execute safety control similarly to the embodiment described earlier. However, in the master-slave method, the user does not touch the arm section of the support arm apparatus directly, and thus when the motion restriction is executed, there is a concern that the user may have difficulty grasping the motion restriction intuitively. Consequently, in the case in which the support system is applied to a support arm apparatus of the master-slave method, it is preferable that the user be notified more actively that the motion restriction is executed.

For example, feedback corresponding to the motion restriction may be executed with respect to a controller by which the user executes operation input. Specifically, in the case in which the motion speed of the arm section is restricted, in accordance with the motion speed, a sense of resistance may be applied to the motion of an operating body, such as a joystick operated by the user. Alternatively, in the case in which the operation of the arm section is stopped, the operating body operated by the user may also be locked correspondingly and cease to move. Furthermore, the controller may also vibrate together with such application of a sense of resistance to the operating body or the locking of the operating body. By providing the user with various feedback corresponding to the motion restriction in this way, the user becomes able to grasp more intuitively that the motion restriction is being executed.

(5-5. Utilization of 3D Model)

When computing the lens tube-biological tissue distance in the embodiment described earlier, a 3D model of biological tissue inside the body cavity as described in Patent Literature 1 above, for example, may also be used in parallel. For example, the support system according to a modification that uses a 3D model in parallel may be realized by additionally providing the support system 1 illustrated in FIG. 2 with a storage section that stores three-dimensional information about biological tissue inside the body cavity of the patent for constructing a 3D model.

For example, in the support system according to the present modification, three-dimensional information indicating the positions and shapes of biological tissues inside the body cavity of the patient is generated on the basis of information obtained by MRI or CT executed on the patient before surgery. The three-dimensional information is stored in the above storage section, and the support system is capable of accessing the three-dimensional information as appropriate.

Herein, in the present modification, the lens tube-biological tissue distance can be detected in real time inside the body cavity of the patient. Utilizing the above, the three-dimensional information stored in the storage section is continuously updated during surgery according to the detected lens tube-biological tissue distance. Since the position of the lens tube is computable on the basis of the information indicating the state of the arm section provided from the arm control section, the safety control section is able to construct an up-to-date 3D model of the biological tissue from the updated three-dimensional information, and by combining the computed position of the lens tube with the constructed 3D model and the detected lens, the safety control section is able to identify the positional relationship between the lens tube and the biological tissues surrounding the lens tube. Additionally, in accordance with the positional relationship, the safety control section is able to appropriately issue the motion-restricting instruction and the warning instruction, similarly to the embodiment described above.

Herein, in the technology described in Patent Literature 1 above, since a 3D model constructed on the basis of three-dimensional information acquired before surgery is used to compute the distance between the lens tube and biological tissue, there is a possibility that the position and shape of the living body during actual surgery may not be reflected accurately. In contrast, according to the present modification, as described above, three-dimensional information is updated continuously according to the lens tube-biological tissue distance detected in real time. Consequently, a 3D model of biological tissue that reflects the actual conditions can be constructed, making it possible to identify the distance between the lens tube and the biological tissue more accurately. In this way, by using in parallel a method of grasping the positional relationship between the lens tube and the biological tissue using a 3D model of the biological tissue in the support system according to the present embodiment, it becomes possible to execute a motion restriction and a warning more appropriately, and it becomes possible to provide even safer surgery.

(6. Supplement)

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

For example, in the foregoing embodiment, a case in which the support system according to the present disclosure is applied to the operation of an endoscope in an endoscopic surgery system is described as an example, but the present technology is not limited to such an example. For example, the support system according to the present disclosure may also be applied to other surgical instruments, such as forceps and retractors. In this case, by providing a distance measurement sensor on the front end of these surgical instruments, or by providing a distance measurement sensor at a position where these surgical instruments may be observed from the outside, it is possible to apply the support system according to the modifications described in (5-1. Distance measurement method) above. Additionally, the support system according to the present disclosure may also be applied to a microscope surgery system in which a microscope for enlarged observation of an operating site is supported by a support arm apparatus. In this case, the distance between the microscope and a biological tissue facing opposite the objective lens of the microscope may be detected on the basis of a captured image of the microscope from a stereo camera, a detection value of a distance measurement sensor provided in the microscope, or a detection value provided at a position where the microscope may be observed from the outside, and safety control may be executed so that the microscope and the biological tissue of the patient do not touch.

Additionally, the present technology may also be configured as below.

(1)

A medical safety control apparatus, in which the medical safety control apparatus issues a motion-restricting instruction for restricting a motion of an arm section of a support arm apparatus that supports a surgical instrument, on a basis of a surgical instrument-biological tissue distance, which is a distance between the surgical instrument and a biological tissue of a patient, the surgical instrument-biological tissue distance being detected while a treatment is being performed on the biological tissue by the surgical instrument.

(2)

The medical safety control apparatus according to (1), in which the medical safety control apparatus issues an instruction for stopping the motion of the arm section as the motion-restricting instruction when the surgical instrument-biological tissue distance is a predetermined first restricted distance or less.

(3)

The medical safety control apparatus according to (2), in which the medical safety control apparatus issues an instruction for restricting a motion speed of the arm section to a predetermined value or less as the motion-restricting instruction when the surgical instrument-biological tissue distance is a predetermined second restricted distance or less, the second restricted distance being greater than the first restricted distance.

(4)

The medical safety control apparatus according to (3), in which the predetermined value that restricts the motion speed of the arm section changes according to the surgical instrument-biological tissue distance.

(5)

The medical safety control apparatus according to (1), 3 or 4, in which the medical safety control apparatus issues an instruction for causing the arm section to execute a retracting motion by which the surgical instrument moves away from the biological tissue as the motion-restricting instruction when the surgical instrument-biological tissue distance is a predetermined first restricted distance or less.

(6)

The medical safety control apparatus according to (5), in which in the retracting motion, the surgical instrument moves backward along a path on which the surgical instrument has advanced.

(7)

The medical safety control apparatus according to any one of (1) to (6), in which the medical safety control apparatus additionally issues an instruction for issuing a warning on the basis of the surgical instrument-biological tissue distance.

(8)

The medical safety control apparatus according to (7), in which the warning is set in stages according to the surgical instrument-biological tissue distance.

(9)

The medical safety control apparatus according to any one of (1) to (8), in which the surgical instrument is an endoscope configured as a stereo camera, and the surgical instrument-biological tissue distance is detected on a basis of a captured image by the endoscope.

(10)

The medical safety control apparatus according to (9), in which a distribution of the surgical instrument-biological tissue distance in a plane approximately perpendicular to an advancement direction of the surgical instrument is detected, and the medical safety control apparatus issues the motion-restricting instruction on the basis of the surgical instrument-biological tissue distance in each of multiple regions set in the advancement direction of the surgical instrument.

(11)

The medical safety control apparatus according to any one of (1) to (8), in which the surgical instrument-biological tissue distance is detected by a distance measurement sensor provided on a front end of the surgical instrument.

(12)

The medical safety control apparatus according to any one of (1) to (8), in which the surgical instrument-biological tissue distance is detected by a distance detection section provided at a position where the surgical instrument and the biological tissue are observable.

(13)

The medical safety control apparatus according to any one of (1) to (12), in which a condition that stipulates a restriction on the motion of the arm section is set in accordance with input made by a user through an NUI.

(14)

The medical safety control apparatus according to (13), in which the input made through the NUI is executed by at least one of speech of the user, a movement of a gaze of the user, a movement of a head of the user, and a gesture of the user.

(15)

The medical safety control apparatus according to any one of (1) to (14), in which a power assist control, in which the arm section is driven in response to an external force imparted to the arm section by a user, is executed with respect to the arm section.

(16)

A medical safety control method including:

issuing a motion-restricting instruction for restricting a motion of an arm section of a support arm apparatus that supports a surgical instrument, on a basis of a surgical instrument-biological tissue distance, which is a distance between the surgical instrument and a biological tissue of a patient, the surgical instrument-biological tissue distance being detected while a treatment is being performed on the biological tissue by the surgical instrument.

(17)
A medical support system including:
a support arm section that supports a surgical instrument with an arm section;
an arm control section that controls a driving of the support arm section; and
a medical safety control section that issues, to the arm control section, a motion-restricting instruction for restricting a motion of the arm section, on a basis of a surgical instrument-biological tissue distance, which is a distance between the surgical instrument and a biological tissue of a patient, the surgical instrument-biological tissue distance being detected while a treatment is being performed on the biological tissue by the surgical instrument.

REFERENCE SIGNS LIST 1, 1a, 1b, 1c support system
110 endoscope section
120 support arm section
130 arm control section
140 image processing distance computation section
150 input section
151 speech detection section
152 gaze detection section
153 head tracking detection section
154 gesture detection section
155 apparatus operation detection section
160 output section
170 safety control section
180a, 180b distance detection section
181 imaging control section
182 display control section
3000 endoscopic surgery system
3100 endoscope
3300 support arm apparatus 3300
3401 CCU
3403 display apparatus
3407 arm control apparatus
3408 safety control apparatus
3409 input apparatus

The invention claimed is:

1. A medical safety control apparatus, comprising:
processing circuitry configured to
obtain a surgical instrument-biological tissue distance, which is a distance between a surgical instrument and a biological tissue of a patient, the surgical instrument-biological tissue distance being detected while a treatment is being performed on the biological tissue by the surgical instrument, the surgical instrument being an endoscope having a lens tube;
determine whether the surgical instrument-biological tissue distance is greater than a predetermined first restricted distance in an advancement region, the advancement region being a cylindrical region in an advancement direction of the lens tube, the cylindrical region having a diameter that is larger than an outer diameter of the lens tube;
in response to determining that the surgical instrument-biological tissue distance is not greater than the predetermined first restricted distance in the advancement region, issue an instruction for stopping a motion of an arm of a support arm apparatus that supports the surgical instrument, or an instruction for causing the arm to execute a retracting motion by which the surgical instrument moves away from the biological tissue;
in response to determining that the surgical instrument-biological tissue distance is greater than the predetermined first restricted distance in the advancement region, determine whether the surgical instrument-biological tissue distance is greater than a predetermined second restricted distance in the advancement region, the second restricted distance being greater than the first restricted distance;
in response to determining that the surgical instrument-biological tissue distance is not greater than the predetermined second restricted distance in the advancement region, issue a first instruction for restricting a motion speed of the arm;
in response to determining that the surgical instrument-biological tissue distance is greater than the predetermined second restricted distance in the advancement region, determine whether the surgical instrument-biological tissue distance is greater than the predetermined first restricted distance in a peripheral region, the peripheral region being a hollow cylindrical region surrounding a periphery of the advancement region; and
in response to determining that the surgical instrument-biological tissue distance is not greater than the predetermined first restricted distance in the peripheral region, issue a second instruction for restricting the motion speed of the arm.

2. The medical safety control apparatus according to claim 1, wherein
the processing circuitry is configured to issue the first instruction for restricting the motion speed of the arm to a predetermined value or less, and
the predetermined value changes according to the surgical instrument-biological tissue distance.

3. The medical safety control apparatus according to claim 1, wherein
in the retracting motion, the surgical instrument moves backward along a path on which the surgical instrument has advanced.

4. The medical safety control apparatus according to claim 1, wherein
the processing circuitry is configured to issue an instruction for issuing a warning based on the surgical instrument-biological tissue distance.

5. The medical safety control apparatus according to claim 4, wherein
the warning is set in stages according to the surgical instrument-biological tissue distance.

6. The medical safety control apparatus according to claim 1, wherein
the endoscope is configured as a stereo camera, and
the surgical instrument-biological tissue distance is detected on a basis of a captured image by the endoscope.

7. The medical safety control apparatus according to claim 6, wherein
the processing circuitry is configured to:
obtain a two-dimensional distribution of the surgical instrument-biological tissue distance in a plane approximately perpendicular to an advancement direction of the surgical instrument; and
issue a motion-restricting instruction for restricting the motion of the arm based on the surgical instrument-biological tissue distance in each of multiple regions set in the advancement direction of the surgical instrument.

8. The medical safety control apparatus according to claim 1, wherein
the surgical instrument-biological tissue distance is detected by a distance measurement sensor provided on a front end of the surgical instrument.

9. The medical safety control apparatus according to claim 1, wherein
the surgical instrument-biological tissue distance is detected by a distance detection section provided at a position where the surgical instrument and the biological tissue are observable.

10. The medical safety control apparatus according to claim 1, wherein
a condition that stipulates a restriction on the motion of the arm is set in accordance with input from a user.

11. The medical safety control apparatus according to claim 10, wherein
the input from the user is executed by at least one of speech of the user, a movement of a gaze of the user, a movement of a head of the user, and a gesture of the user.

12. The medical safety control apparatus according to claim 1, wherein
the processing circuitry is configured to perform a power assist control, in which the arm is driven by an actuator in response to an external force imparted to the arm by a user.

13. A medical safety control method comprising:
obtaining a surgical instrument-biological tissue distance, which is a distance between a surgical instrument and a biological tissue of a patient, the surgical instrument-biological tissue distance being detected while a treatment is being performed on the biological tissue by the surgical instrument, the surgical instrument being an endoscope having a lens tube;
determining, using processing circuitry, whether the surgical instrument-biological tissue distance is greater than a predetermined first restricted distance in an advancement region, the advancement region being a cylindrical region in an advancement direction of the lens tube, the cylindrical region having a diameter that is larger than an outer diameter of the lens tube;
in response to determining that the surgical instrument-biological tissue distance is not greater than the predetermined first restricted distance in the advancement region, issuing an instruction for stopping a motion of an arm of a support arm apparatus that supports the surgical instrument, or an instruction for causing the arm to execute a retracting motion by which the surgical instrument moves away from the biological tissue;
in response to determining that the surgical instrument-biological tissue distance is greater than the predetermined first restricted distance in the advancement region, determining, using the processing circuitry, whether the surgical instrument-biological tissue distance is greater than a predetermined second restricted distance in the advancement region, the second restricted distance being greater than the first restricted distance;
in response to determining that the surgical instrument-biological tissue distance is not greater than the predetermined second restricted distance in the advancement region, issuing a first instruction for restricting a motion speed of the arm;
in response to determining that the surgical instrument-biological tissue distance is greater than the predetermined second restricted distance in the advancement region, determining, using the processing circuitry, whether the surgical instrument-biological tissue distance is greater than the predetermined first restricted distance in a peripheral region, the peripheral region being a hollow cylindrical region surrounding a periphery of the advancement region; and
in response to determining that the surgical instrument-biological tissue distance is not greater than the predetermined first restricted distance in the peripheral region, issuing a second instruction for restricting the motion speed of the arm.

14. A medical support system comprising:
a support arm apparatus that supports a surgical instrument with an arm; and
processing circuitry configured to
control a driving of the support arm apparatus;
obtain a surgical instrument-biological tissue distance, which is a distance between the surgical instrument and a biological tissue of a patient, the surgical instrument-biological tissue distance being detected while a treatment is being performed on the biological tissue by the surgical instrument, the surgical instrument being an endoscope having a lens tube;
determine whether the surgical instrument-biological tissue distance is greater than a predetermined first restricted distance in an advancement region, the advancement region being a cylindrical region in an advancement direction of the lens tube, the cylindrical region having a diameter that is larger than an outer diameter of the lens tube;
in response to determining that the surgical instrument-biological tissue distance is not greater than the predetermined first restricted distance in the advancement region, issue an instruction for stopping a motion of the arm of the support arm apparatus that supports the surgical instrument, or an instruction for causing the arm to execute a retracting motion by which the surgical instrument moves away from the biological tissue;
in response to determining that the surgical instrument-biological tissue distance is greater than the predetermined first restricted distance in the advancement region, determine whether the surgical instrument-biological tissue distance is greater than a predetermined second restricted distance in the advancement region, the second restricted distance being greater than the first restricted distance;
in response to determining that the surgical instrument-biological tissue distance is not greater than the predetermined second restricted distance in the advancement region, issue a first instruction for restricting a motion speed of the arm;
in response to determining that the surgical instrument-biological tissue distance is greater than the predetermined second restricted distance in the advancement region, determine whether the surgical instrument-biological tissue distance is greater than the predetermined first restricted distance in a peripheral region, the peripheral region being a hollow cylindrical region surrounding a periphery of the advancement region; and
in response to determining that the surgical instrument-biological tissue distance is not greater than the predetermined first restricted distance in the peripheral region, issue a second instruction for restricting the motion speed of the arm.

* * * * *